(12) United States Patent
Riscoe et al.

(10) Patent No.: US 8,987,296 B2
(45) Date of Patent: *Mar. 24, 2015

(54) ACRIDONE COMPOUNDS

(71) Applicants:Oregon Health & Science University, Portland, OR (US); The United States of America DBA The Department of Veterans Affairs, Washington, DC (US)

(72) Inventors: Michael K. Riscoe, Tualatin, OR (US); Rolf W. Winter, Portland, OR (US); Jane X. Kelly, Portland, OR (US); David J. Hinrichs, Lake Oswego, OR (US); Martin J. Smilkstein, Portland, OR (US)

(73) Assignees: Oregon Health & Science University, Portland, OR (US); The United States of America DBA The Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/066,565

(22) Filed: Oct. 29, 2013

(65) Prior Publication Data

US 2014/0128423 A1 May 8, 2014

Related U.S. Application Data

(62) Division of application No. 12/312,503, filed as application No. PCT/US2007/084560 on Nov. 13, 2007, now Pat. No. 8,592,447.

(60) Provisional application No. 60/858,802, filed on Nov. 13, 2006.

(51) Int. Cl.
*A61K 31/44* (2006.01)
*C07D 219/04* (2006.01)
*C07D 219/06* (2006.01)
*C07D 401/06* (2006.01)
*C07D 219/14* (2006.01)

(52) U.S. Cl.
CPC ............ *C07D 219/06* (2013.01); *C07D 401/06* (2013.01); *C07D 219/14* (2013.01)
USPC .......................................... 514/297; 546/103

(58) Field of Classification Search
None
See application file for complete search history.

(56) References Cited

U.S. PATENT DOCUMENTS

| 2,647,901 | A | 8/1953 | Archer |
| 2,709,171 | A | 5/1955 | Stoughton |
| 2,732,373 | A | 1/1956 | Steiger |
| 2,732,374 | A | 1/1956 | Steiger |
| 3,981,903 | A | 9/1976 | Hirano et al. |
| 4,150,134 | A | 4/1979 | Schulenberg |
| 4,244,954 | A | 1/1981 | Schulenberg |
| 4,250,182 | A | 2/1981 | Garvin |
| 5,977,077 | A | 11/1999 | Winter et al. |
| 6,143,737 | A | 11/2000 | Clarke et al. |
| 6,248,891 | B1 | 6/2001 | Sharp et al. |
| 6,541,483 | B2 | 4/2003 | Michejda et al. |
| 6,613,797 | B2 | 9/2003 | Winter et al. |
| 6,686,469 | B2 | 2/2004 | Eberle et al. |
| 6,703,388 | B2 | 3/2004 | Miyamoto et al. |
| 6,800,618 | B2 | 10/2004 | Lin et al. |
| 2002/0055644 | A1 | 5/2002 | Winter et al. |
| 2005/0171079 | A1 | 8/2005 | Schrimpf et al. |

FOREIGN PATENT DOCUMENTS

| CA | 1258854 | 8/1989 |
| DE | 551029 | 5/1932 |
| EP | 0 110 298 A1 | 11/1983 |

OTHER PUBLICATIONS

Rolf et al., "Evaluation and lead optimization of anti-malarial acridones," Experimental Parasitology, 114 (2006) 47-56—Available online Jul. 7, 2006.*
Adams et al., "The Iron Environment in Heme and Heme-Antimalarial Complexes of Pharmacological Interest," *Journal of Inorganic Biochemistry* 63:69-77, 1996.
Ager et al., "Rodent Malaria Models," 68/1:225-264, Springer-Verlag, Berlin, 1984.
Ahmed et al., "A new rapid and simple non-radioactive assay to monitor and determine the proliferation of lymphocytes: an alternative to [$^3$H]thymidine incorporation assay," *Journal of Immunological Methods*170:211-224, 1994.
Ahua et al., "Antileishmanial and antifungal acridone derivatives from the roots of *Thamnosma rhodesic*," *Phytochemistry* 65:963-968, 2004.
Anderson et al., "Parallel synthesis of 0-aminoacridines and their evaluation against chloroquine-resistant *Plasmodium falciparum*," *Bioorganic & Medicinal Chemistry* 14:334-343, 2006.
Atkinson et al., "Ultrastructure of Malaria-Infected Erythrocytes," *Blood Cells* 16:351-368, 1990.
Bastow, "New Acridone Inhibitors of Human Herpes Virus Replication," *Current Drug Targets—Infectious Disorders* 4:323-330, 2004.
Bojang et al., "Follow-up of Gambian children recruited to a pilot safety and immunogenicity study of the malaria vaccine SPf66," *Parasite Immunology* 19(12):579-581, 1997.
Boudreau et al., "Tolerability of prophylactic Lariam® regimens," *Trop. Med. Parasitol.* 44:257-265, 1993.
Brewer et al., "Factors Relating to Neurotoxicity of Artemisinin Antimalarial Drugs 'Listening to Arteether,'" *Med Trop* 58(Supp 3):22S-27S, 1998.

(Continued)

*Primary Examiner* — Sreeni Padmanabhan
*Assistant Examiner* — Jody Karol
(74) *Attorney, Agent, or Firm* — Klarquist Sparkman, LLP

(57) ABSTRACT

A class of acridone compounds has been discovered that exhibits chemosensitizing and antiparasitic activity. Described herein are pharmaceutical compositions and methods for their use to treat parasitic infections, such as malaria and toxoplasmosis, and to sensitize resistant cells, such as multidrug resistant cells to other therapeutic agents. The pharmaceutical compositions and methods may also be used to treat and/or prevent psychotic diseases such as schizophrenia.

27 Claims, 8 Drawing Sheets

(56) References Cited

OTHER PUBLICATIONS

Brewer et al., "Neurotoxicity in animals due to arteether and artemether," *Transactions of the Royal Society of Tropical Medicine and Hygiene* 88(Supp 1):33-36, 1994.
Broudy et al., "Monocytes Stimulate Fibroblasoid Bone Marrow Stromal Cells to Produce Multilineage Hematopoietic Growth Factors," *Blood* 68(2):530-534, Aug. 1986.
Carter et al., "Evolutionary and Historical Aspects of the Burden of Malaria," *Clinical Microbiology Reviews* 15(4):564-594, Oct. 2002.
Clark et al., "Developmental Toxicity of Artesunate and an Artesunate Combination in the Rat and Rabbit," *Birth Defects Research (Part B)* 71:380-394, 2004.
Coleman et al., "Gametocytocidal and Sporontocidal Activity of Antimalarials Against *Plasmodium berghei Anka* in ICR Mice and *Anopheles stephensi* Mosquitoes," *Am. J. Trop. Med. Hyg.* 46(2):169-182 1992.
Croft et al., "The activity of hydroxynaphthoquinones against *Leishmania donovani*," *Journal of Antimicrobial Chemotherapy* 30:827-832, 1992.
De Silva et al., "Luminescence Determination of Pharmaceuticals of the Tetrahydrocarbazole, Carbazole, and 1,4-Benzodiazepine Class," *Analytical Chemistr*, 48(1):144-155, 1976.
Doolan et al., "DNA Vaccination as an Approach to Malaria Control: Current Status and Strategies," *Curr. Top Microbial. Immunol.* 226:37-58, 1998.
Fidock et al., "Antimalarial Drug Discovery: Efficacy Models for Compound Screening," *Nature Reviews / Drug Discovery* 3:509-520, Jun. 2004.
Fivelman et al., "Modified Fixed-Ratio Isobologram Method for Studying In Vitro Interactions between Atovaquone and Proguanil or Dihydroartemisinin against Drug-Resistant Strains of *Plasmodium falciparum*," *Antimicrobial Agents and Chemotherapy* 48(11):4097-4102, Nov. 2004.
Fujioka et al., "Activities of New Acridone Alkaloid Derivatives against *Plasmodium yoelii* in vitro," *Arzneim. Forsch. /Drug Res.* 40(11)(9):1026-1029, 1990.
Fusetti et al., "Meflochina ed ototossicita: descrizione di tres casi," *Clin Ther* 150:379-382, 1999.
Galey et al., "A Convenient Synthesis of *N*-Alkylacridanones Using Phase-Transfer Catalysis," *Synthesis* 12:944-946, 1979.
Guillouzo, "Liver Cell Models in in Vitro Toxicology," *Environmental Health Perspectives* 106(Supp 2):511-532, 1998.
Hedge et al., "Anti-calmodulin acridone derivatives modulate vinblastine resistance in multidrug resistant (MDR) cancer cells," *European Journal of Medicinal Chemistry*, 39:161-177, 2004.
Horio et al., "ATP-dependent transport of vinblastine in vesicles from human multidrug-resistant cells," *Proc. Natl. Acad. Sci.*, 85:3580-3584, 1988.
Hudson et al., "566C80: A Potent Broad Spectrum Anti-Inflective Agent with Activity Against Malaria and Opportunistic Infections in AIDS Patients," *Drugs Exptl. Clin. Res.* XVII(9):427-435, 1991.
Hudson, "Atovaquone—A Novel Broad-spectrum Anti-infective Drug," *Parasitology Today* 9(2):66-68, 1993.
Ignatushchenko et al., "Xanthones as Antimalarial Agents: Stage Specificity," *Am. J. Trop. Med. Hyg.* 62(1):77-81, 2000.
Ignatushchenko et al., "Xanthones as antimalarial agents; studies of a possible mode of action," *FEBS Letters* 409:67-73, 1997.
Kelly et al., "A spectroscopic investigation of the binding interaction between 4,5-dihydroxyxanthone and heme," *Journal of Inorganic Biochemistry* 86:617-625, 2001.
Kelly et al., "Antileishmanial drug development: exploitation of parasite heme dependency," *Mol Biochem Parasitol* 126(1):43-49, 2003.
Kelly et al., "Discovery of dual function acridones as a new antimalarial chemotype," *Nature*, published online Apr. 8, 2009.
Kelly et al., "Optimization of Xanthones for Antimalarial Activity: the 3,6-Bis-ω-Diethylaminoalkoxyxanthone Series," *Antimicrobial Agents and Chemotherapy* 46(1):144-150, Jan. 2002.
Kelly et al., "Orally Active Acridones as Novel and Potent Antimalarial Chemotypes," Abstract, *ASTMH 55th Annual Meeting*, Atlanta, Georgia, 1 page (Nov. 12-16, 2006).

Kelly et al., "Structure-Activity Relationships of Orally Active Antimalarial Acridones: Synthesis, Optimization, and Biological Activity," Abstract, *ASTMH 55th Annual Meeting*, Atlanta, Georgia, 1 page (Nov. 12-16, 2006).
Kelly et al., "The kinetics of uptake and accumulation of 3,6-bix-ω-diethylamino-amyloxyxanthone by the human malaria parasite *Plasmodium falciparum*," *Molecular and Biochemical Parasitology* 123:47-54, 2002.
Kessl et al., "Cytochrome *b* Mutations that Modify the Ubiquinol-binding Pocket of the Cytochrome $bc_1$ Complex and Confer Antimalarial Drug Resistance in *Saccharomyces cerevisiae*," *The Journal of Biological Chemistry* 280(17): 17142- 17148, Apr. 29, 2005.
Kessl et al., "Molecular Basis for Atovaquone Resistance in *Pleumocystis jirovecii* Modeled in the Cytochrome $bc_1$ Complex of *Saccharomyces cervisiae*," *The Journal of Biological Chemistry* 279(4):2817-2824, Jan. 23, 2004.
Korsinczky et al., "Mutations in *Plasmodium falciparum* Cytochrome *b* That Are Associated with Atovaquone Resistance Are Located at a Putative Drug-Binding Site," *Antimicrobial Agents and Chemotherapy* 44(8):2100-2108, Aug. 2000.
Krungkrai, "The multiple roles of the mitochondrion of the malarial parasite," *Parasitology* 129:51-524, 2004.
Learngaramkul et al., "Molecular Characterization of Mitochondria in Asexual and Sexual Blood Stages of *Plasmodium falciparum*," *Molecular Cell Biology Research Communications* 2(1):15-20, 1999.
Li et al., "Cryopreserved human hepatocytes: characterization of drug-metabolizing enzyme activities and applications in higher throughput screening assays for hepatotoxicity, metabolic stability, and drug-drug interaction potential," *Chemico-Biological Interactions* 121:17-35, 1999.
Low, "Chapter 3: Metabolic Changes of Drugs and Related Organic Compounds," *Wilson and Gisvold's Textbook of Organic Medicinal and Pharmaceutical Chemistry, 10th Edition* (Delgado and Remers, eds.), pp. 43-122, Lippincott—Raven Publishers, Philadelphia, PA, 1998.
Lowden et al., "Cell culture replication of herpes simplex virus and, or human *Cytomegalovirus* is inhibited by 3,7-dialkoxylated, 1-hydroxyacridone derivatives," *Antiviral Research* 59:143-154, 2003.
Luzzi et al., "Adverse Effects of Antimalarials, an Update," *Drug Safety* 8(4):295-311, 1993.
Madan et al., "Effect of Cryopreservation on Cytochrome P-450 Enzyme Induction in Cultured Rat Hepatocytes," *Drug Metabolism and Disposition* 27(3):327-335, 1999.
Makler et al., "Detection of *Plasmodium falciparum* Infection with the Fluorescent Dye, Benzothiocarboxypurine," *American Journal of Tropical Medicine and Hygiene* 44(1):11-16, 1991.
Meshnick et al., "Multiple Cytochrome b Mutations May Cause Atovaquone Resistance," *The Journal of Infectious Diseases* 191:822-823, 2005.
Michael, "Quinoline, quinazoline and acridone alkaloids," *Nat. Prod. Rep.* 18:543-559, 2001.
Michael, "Quinoline, quinazoline and acridone alkaloids," *Nat. Prod Rep.* 20:476-493, 2003.
Milhous, "Development of New Drugs for Chemoprophylaxis of Malaria," *Med. Trop.* 61(1):48-50, 2001.
Oettmeier et al., "Inhibition of electron transport through the $Q_p$ site in cytochrome $b/c_1$ complexes by acridones," *Biochimica et Biophysica Acta* 1188:125-130, 1994.
Olliaro et al., "An Overview of Chemotherapeutic Targets for Antimalarial Drug Recovery," *Pharmacol. Ther.* 81(2):91-110, 1999.
Pessina et al., "Application of the CFU-GM Assay to Predict Acute Drug-Induced Neutropenia: An International Blind Trial to Validate a Prediction Model for the Maximum Tolerated Dose (MTD) of Myelosuppressive Xenobiotics," *Toxicological Sciences* 75:355-367, 2003.
Pessina et al., "In Vitro Tests for Haematotoxicity: Prediction of Drug-induced Myelosuppression by the CFU-GM Assay," *Alta* 32(Supp. 2):75-79, 2002.

(56) References Cited

OTHER PUBLICATIONS

Peters et al., "The chemotherapy of rodent malaria, XXIII, Casual prophylaxis, part II: Practical experience with *Plasmodium youlii nigeriensis* in drug screening," *Annals of Topical Medicine and Parasitology* 69(3):311-328, 1975.
Phillips-Howard et al., "CNS Adverse Events Associated With Antimalarial Agents," *Drug Safety* 12(6):370-383, 1995.
Raether et al., "Action of a New Floxacrine Derivative (S 82 5455) on Asexual Stages of *Plasmodium berghei*: A Light and Electron Microscopical Study," *Zbl. Bakt. Hyg. A* 256:335-341, 1984.
Raether et al., "Antimalarial activity of Floxacrine (HOE 991) I: Studies on blood schizontocidal action of Floxacrine against *Plasmodium berghei, P. vinckei* and *P. cynomolgi*," *Annals of Tropical Medicine and Parasitology* 73(6):505-526, 1979.
Rathbun et al., "Interferon-γ-induced apoptotic responses of Fanconi Anemia group C hemapopoietic progenitor cells involve caspase 8-dependent activation of caspase 3 family members," *Blood* 96(13):4204-4211, Dec. 15, 2000.
Riscoe et al., "Evaluation and Lead Optimization of Antimalarial Aromatic Ketones," Abstract, *ASTMH 55th Annual Meeting*, Atlanta, Georgia, 1 page (Nov. 12-16, 2006).
Sachs et al., "The economic and social burden of malaria," *Nature* 415:680-685, Feb. 2002.
Schmidt, "Antimalarial Properties of Floxacrine, a Dihydroacridinedione Derivative," *Antimicrobial Agents and Chemotherapy* 16(4):475-485, Oct. 1979.
Singh et al., "Interaction between chloroquine and diverse pharmacological agents in chloroquine resistant *Plasmodium yoelii nigeriensis*," *Acta Tropica* 77:1185-193, 2000.
Slomianny et al., "A Cytochemical Ultrastructural Study of the Lysosomal System of Different Species of Malaria Parasites," *J. Protozool.* 37(6):465-470, 1990.
Smilkstein et al., "Novel Antimalarial Acridone Derivatives with Both Intrinsic Potency and Synergy with Selected Quinolines: In Vitro and In Vivo Studies," Abstract, ASTMH 55th Annual Meeting, Atlanta, Georgia, 1 page (Nov. 12-16, 2006).
Smilkstein et al., "Simple and Inexpensive Fluorescence-Based Technique for High-Throughput Antimalarial Drug Screening," *Antimicrobial Agents and Chemotherapy* 48(5):1803-1806, May 2004.
Srivastava et al., "Atovaquone, a Broad Spectrum Antiparasitic Drug, Collapses Mitochondrial Membrane Potential in a Malarial Parasite," *The Journal of Biological Chemistry* 272(7):3961-3966, 1997.
Srivastava et al., "Resistance mutations reveal the atovaquone-binding domain of cytochrome *b* in malaria parasites," *Molecular Microbiology* 33(4):704-7114, 1999.
Suswam et al., "*Plasmodium falciparum*: The Effects of Atovaquone Resistance on Respiration," *Experimental Parasitology* 98:180-187, 2001.
Taylor et al, "Antimalarial Drug Toxicity," *Drug Safety* 27(1):25-61, 2004.
Toovey et al., "Audiometric changes associated with the treatment of uncomplicated falciparum malaria with co-artemether," *Transactions of the Royal Society of Tropical Medicine and Hygiene* 98:261-267, 2004.
Torrey et al., "*Taxoplasma* gondii and Schizophrenia," *Emerging Infectious Diseases*, 9(11):1375-1382, Nov. 2003.
Trouiller et al., "Drug Development Output from 1975 to 1996: What Proportion for Tropical Diseases?" *Int. J. Infect. Dis.* 3:61-63, 1998.
Trouiller et al., "Drug development output: what proportion for tropical diseases?" *The Lancet* 354:164, Jul. 10, 1999.
Turker, "Estimation of mutation frequencies in normal mammalian cells and the development of cancer," *Cancer Biology* 8:407-419, 1998.
Vaidya et al., "Atovaquone resistance in malarial parasites," *Drug Resistance Updates*3:283-287 , 2000.
Vaidya, "Chapter 25: Mitochondrial Physiology as a Target for Atovaquone and Other Antimalarials," *Malaria Parasite Biology, Pathogenesis, and Protection* (Irwin W. Sherman, ed.), pp. 355-368, ASM Press, Washington, D.C., 1998.
Varney et al., "Long-Term Neuropsychological Sequelae of Fever Associated With Amnesia," *Archives of Clinical Neuropsychology* 9(4):347-352, 1994.
Varney et al., "Neuropsychiatric Sequelae of Cerebral Malaria in Vietnam Veterans," *The Journal of Nervous and Mental Disorders* 185:695-703, 1997.
Via et al., "Effects of cytokines on mycobacterial phagosome maturation," *Journal of Cell Science* 111:897-905, 1998.
Weina, "From Atabrine in World War II to Mefloquine in Somalia: The Role of Education in Preventative Medicine," *Military Medicine* 163:635-639, 1998.
White et al., "Averting a malaria disaster," *The Lancet* 353:1965-1967, Jun. 5, 1999.
White, "Antimalarial drug resistance," *The Journal of Clinical Investigation* 113(8):1084-1092, Apr. 2004.
Winkelmann et al., "Antimalarial and Anticoccidial Activity of 3-Aryl-7-chloro-3,4-dihydroacridine-1,9-(2H, 10H)-diones," *Arzneim. Forsch. / Drug Res.* 37(1)(6):647-661, 1987.
Winstanley et al., "Comment on: Audiometric changes associated with the treatment of uncomplicated falciparum malaria with co-artemether," *Transactions of the Royal Society of Tropical Medicine and Hygiene* 98:268-268, 2004.
Winter et al., "Antimalarial quinolones: Synthesis, potency, and mechanistic studies," *Experimental Parasitology* 118(4):487-497, Apr. 2008.
International Search Report dated Mar. 31, 2008 in International Application No. PCT/US2007/084660.

\* cited by examiner

Exhibit B

Exhibit B

Exhibit B

ACRIDONE COMPOUNDS

CROSS-REFERENCE TO RELATED APPLICATIONS

This application claims the benefit of the earlier filing date of U.S. Provisional Application No. 60/858,802, which is incorporated herein by reference in its entirety.

FIELD

This disclosure concerns acridone compounds, compositions and methods for their use as antiparasitic agents, antipsychotic agents, and chemo sensitizers.

BACKGROUND

Throughout human history malaria has plagued mankind. Malaria remains the single most devastating parasitic infectious agent in the world, particularly in the developing and tropical world. Malaria infects hundreds of millions and kills roughly 2 million people each year. Globally the situation is worsening, largely due to the emergence of multidrug resistant strains of the responsible parasite.

In the past, the inexpensive, effective and orally available antimalarial drug, chloroquine, was the "gold standard" treatment. Unfortunately, certain Plasmodium sp. strains have evolved resistance to chloroquine. In fact, the spread of chloroquine-resistant Plasmodium sp. parasites has rendered chloroquine almost useless for malaria treatment. Multidrug resistant strains no longer susceptible to quinoline and antifolate-based antimalarials are common in Southeast Asia and some parts of Africa. In addition, Plasmodium sp. resistance to other antimalarial drugs, such as artemisinin and its derivatives, has been reported. These are particularly devastating problems in many impoverished parts of the world where such drugs are most needed.

Multidrug resistance is a phenomenon which has been observed in cancer and in and other conditions, such as bacterial, viral, protozoal, and fungal diseases. Multidrug resistance is a particular problem in diseases such as malaria, tuberculosis, Entamoeba histolytica (amoebic dysentery), trypanosomiasis (African sleeping sickness), leishmaniasis and AIDS pneumonia, among others. A number of diverse drugs have been found effective against such diseases, but in multidrug resistance a disease becomes resistant to a variety of drugs to which it initially was susceptible. In many examples, multidrug resistance renders drugs that worked initially totally ineffective. Thus, there is a need not only for new antimalarial drugs, but also for new drugs to treat multidrug resistance.

Parasitic diseases have also been associated with psychotic diseases such as schizophrenia. In other words, parasitic infection in a subject could result in schizophrenia and schizophrenic symptoms. There exists a continued need for anti-psychotic drugs.

SUMMARY

This disclosure concerns the discovery of a class of acridone compounds. This class of compounds exhibits chemosensitizing and antiparasitic activity. Exemplary chemosensitizing and antiparasitic acridones disclosed herein include those represented by the formula:

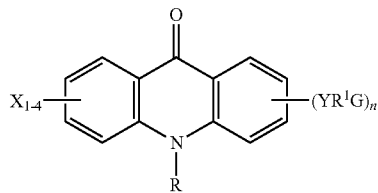

or a pharmaceutically acceptable salt thereof;
wherein R is H, —$R^2NR^3R^4$ or —$R^1G$;
X is H, halogen, haloalkyl, $OR^5$ or —$YR^1G$;
n is 0-4;
Y is H, —$CH_2$—, —$CH_2O$—, —O—, —$N(R^6)$— or —S—;
$R^5$ is lower alkyl, haloalkyl or —$R^7NR^8R^9$;
$R^1$, $R^2$ and $R^7$ independently are optionally substituted alkyl;
G is —$NR^{10}R^{11}$, halogen or fluoroalkyl;
$R^3$, $R^4$, $R^6$, $R^8$ and $R^9$ independently are H, lower alkyl, or aralkyl;
$R^{10}$ and $R^{11}$ independently are H, lower alkyl, aralkyl or together form an aliphatic or aromatic ring optionally including one or more additional heteroatoms; and when n is 0, R is —$R^1G$.

Also described are hydrates and pharmaceutically acceptable prodrugs and salts of the acridones above. Moreover, all enantiomeric, diastereomeric and geometric isomeric forms of the disclosed formulas are intended.

Also described are uses of the compounds and methods of administration.

The foregoing and other objects, features, and advantages of the invention will become more apparent from the following detailed description, which proceeds with reference to the accompanying figures.

DETAILED DESCRIPTION

Figure 1:
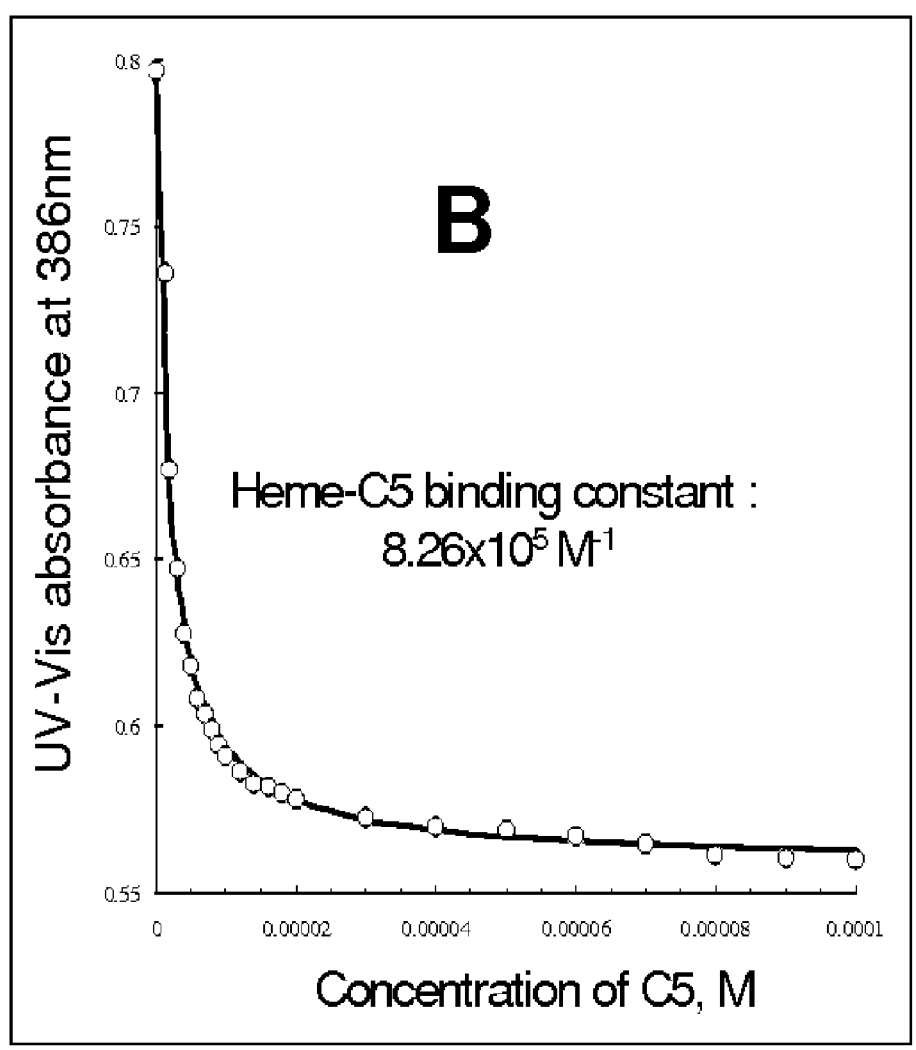
FIG. 1 demonstrates the inhibition of in vitro heme aggregation by xanthone 2,3,4,5,6-pentahydroxyxanthone; panel B illustrates a spectrophotometric titration curve of the heme: 3,6-bis-ε-(N,N-diethylamino)-amyloxy xanthone (C5) complex.

Disclosed herein are recently discovered acridone compounds that are highly effective in reversing multidrug resistance and for directly killing and/or inhibiting the growth of parasites, including multi-drug resistant parasites. Such compounds may be used, at least, in pharmaceutical compositions, and to treat parasitic diseases such as malaria and toxoplasmosis. The compounds may be used to inhibit the growth of organisms such as *Plasmodium* sp., *Toxoplasma gondii, Mycobacterium tuberculosis, Pneumocystis carinii*. In yet other embodiments, any of the foregoing or other disclosed compounds can be incorporated into pharmaceutical compositions that include a therapeutically effective amount of the compound or extract, and a pharmaceutically acceptable carrier. In some instances, a disclosed pharmaceutical composition further includes at least one additional active agent. In certain embodiments the second active agent is an antimalarial therapeutic agent (such as a quinoline compound, e.g. quinine, chloroquine, mefloquine or the like, a peroxide compound, such as an artemisinin, a folate synthesis inhibitor, such as sulfadoxine and/or pyrimethamine, or a cinchona alkaloid, such as quinine, quinidine and the like).

The present disclosure also concerns methods of treating a subject for parasitemia, such as malaria or *Plasmodium* sp. infection by administering to the subject a therapeutically effective amount (such as from about 1 to about 50 mg/kg) of any of the compounds disclosed herein. In some cases, the compound is administered prophylactically. In other embodiments, the malarial pathogen is *P. falciparum*.

Also disclosed are methods for inhibiting the growth of *Plasmodium* sp. involving contacting at least one *Plasmodium* sp. parasite with a growth inhibitory amount (such as from about 0.1 to about 500 nM, such as from about 1 to about 250 nM, in particular from about 5 to about 50 nM) of at least one disclosed compound. In some method embodiments, the *Plasmodium* sp. is *P. falciparum, P. vivax, P. ovale,* or *P. malariae*, or a combination thereof.

The disclosed compounds may be used to inhibit the growth of protozoa such as *Toxoplasma gondii*, bacteria such as *Mycobacterium tuberculosis*, and fungal parasites such as *Pneumocystis carinii*. Treating diseases caused by these parasites is also within the scope of this disclosure. Also encompassed are diseases and conditions caused by *Toxoplasma* sp., *Mycobacterium* sp., and *Pneumocystis* sp.

In some cases the disclosed acridone compounds are used as chemosensitizers to sensitize a resistant cell, for example by reversal of multidrug resistance. Accordingly, further disclosed embodiments include methods for potentiating a drug that has been rendered less effective by resistance, such as multidrug resistance. In these methods a disclosed acridone compound is administered in conjunction with the drug to be potentiated. Classes of drugs whose efficacy can be restored using the disclosed acridones as chemosensitizers include, without limitation, anticancer agents, antibiotics, antiparasitics, antifungals and antivirals.

I. Terms:

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

"Optional" or "optionally" means that the subsequently described event or circumstance can but need not occur, and that the description includes instances where said event or circumstance occurs and instances where it does not.

"Derivative" refers to a compound or portion of a compound that is derived from or is theoretically derivable from a parent compound.

"Subject" includes, without limitation, humans and veterinary subjects, particularly economically important animals, such as livestock and avians, particularly poultry infected with protozoans, such as Eimeria.

The phrase "treating a disease" refers to inhibiting the full development of a disease or condition, for example, in a subject who is at risk for a disease such as trypanasomal infection, for instance a *P. falciparum* infection, particularly a multidrug resistant strain of *P. falciparum*. Other instances of diseases include those caused by *T. gondii, M. tuberculosis,* and *P. carinii*. The phrase "treating a disease" also encompasses diminishing or reversing multidrug resistance, to sensitize a pathogen to a drug to which it has acquired resistance. Multiple drug resistance occurs when target cells, including trypanosome cells, such as *P. falciparum* become resistant to a drug being used during treatment and to other drugs that are different and structurally unrelated to the drug being administered. Certain compounds, including, without limitation verapamil, diltiazem, cyclosporin and catharanthine are known to attenuate or reverse drug resistance in some cells. Such compounds are referred to as "chemosensitizers" or "reversal agents."

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease.

A "prophylactic" treatment is a treatment administered to a subject who does not exhibit signs of a disease or exhibits only early signs for the purpose of decreasing the risk of developing pathology.

By the term "coadminister" is meant that each of at least two compounds be administered during a time frame wherein the respective periods of biological activity overlap. Thus, the term includes sequential as well as coextensive administration of two or more drug compounds.

In one embodiment a "chemosensitizer" or "chemosensitizing agent" or "reversing agent" refers to an agent that diminishes or abolishes resistance to a therapeutic agent. In one embodiment, a chemosensitizer allows the net accumulation of a therapeutic compound in multidrug resistant cells. In some examples, chemosensitizers disclosed herein are effective to result in the accumulation of a therapeutic compound to an equivalent level to the net accumulation of the therapeutic compound in non-multidrug resistant cells. The presence of a chemosensitizer may also merely increase the amount of the therapeutic compound able to accumulate in a multidrug resistant cell compared to the amount accumulated in the absence of the chemosensitizer. The chemosensitizers disclosed herein also operate to reverse other mechanisms of resistance besides multidrug resistance.

The term "neoplasm" refers to an abnormal cellular proliferation, which includes benign and malignant tumors, as well as other proliferative disorders.

The term "acyl" refers group of the formula RC(O)— wherein R is an organic group.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms.

The term "alkenyl" refers to a hydrocarbon group of 2 to 24 carbon atoms and structural formula containing at least one carbon-carbon double bond.

The term "alkynyl" refers to a hydrocarbon group of 2 to 24 carbon atoms and a structural formula containing at least one carbon-carbon triple bond.

The terms "halogenated alkyl" or "haloalkyl group" refer to an alkyl group as defined above with one or more hydrogen atoms present on these groups substituted with a halogen (F, Cl, Br, I).

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The term "aliphatic" is defined as including alkyl, alkenyl, alkynyl, halogenated alkyl and cycloalkyl groups as described above. A "lower aliphatic" group is a branched or unbranched aliphatic group having from 1 to 10 carbon atoms.

The term "aryl" refers to any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted. The term "alkyl amino" refers to alkyl groups as defined above where at least one hydrogen atom is replaced with an amino group.

"Carbonyl" refers to a radical of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine.

"Carboxyl" refers to a —COOH radical. Substituted carboxyl refers to —COOR where R is aliphatic, heteroaliphatic, alkyl, heteroalkyl, or a carboxylic acid or ester.

The term "hydroxyl" is represented by the formula —OH. The term "alkoxy group" is represented by the formula —OR, where R can be an alkyl group, optionally substituted with an alkenyl, alkynyl, aryl, aralkyl, cycloalkyl, halogenated alkyl, or heterocycloalkyl group as described above.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

The term "lower alcohol" refers to an alkyl group containing from one to ten carbon atoms substituted with one or more hydroxy (—OH) moieties. Examples of lower alcohols include, without limitation The term "amine" or "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group described above.

The term "amide group" is represented by the formula —C(O)NRR', where R and R' independently can be a hydrogen, alkyl, alkenyl, alkynyl, aryl, aralkyl, cycloalkyl, halogenated alkyl, or heterocycloalkyl group described above.

The term "aralkyl" refers to an aryl group having an alkyl group, as defined above, attached to the aryl group. An example of an aralkyl group is a benzyl group.

Optionally substituted groups, such as "substituted alkyl," refers to groups, such as an alkyl group, having from 1-5 substituents, typically from 1-3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, optionally substituted heteroaryl, optionally substituted heterocyclyl, hydroxy, thiol and thioalkoxy.

The term "protecting group" or "blocking group" refers to any group that when bound to a functional group.

Reference will now be made in detail to the presently preferred compounds.

II. Chemosensitizing and Antiparasitic Compounds:

In general the acridone compounds disclosed herein can be represented by the formula or a pharmaceutically acceptable salt thereof;

wherein R is H, —$R^2NR^3R^4$ or —$R^1G$;

X is H, halogen, haloalkyl, $OR^5$ or —$YR^1G$;

n is 0-4;

Y is H, —$CH_2$—, —$CH_2O$—, —O—, —$N(R^6)$— or —S—;

$R^5$ is lower alkyl, haloalkyl or —$R^7NR^8R^9$;

$R^1$, $R^2$ and $R^7$ independently are optionally substituted alkyl;

G is —$NR^{10}R^{11}$, halogen or fluoroalkyl;

$R^3$, $R^4$, $R^6$, $R^8$ and $R^9$ independently are H, lower alkyl, or aralkyl;

$R^{10}$ and $R^{11}$ independently are H, lower alkyl, aralkyl or together form an aliphatic or aromatic ring optionally including one or more additional heteroatoms; and when n is 0, R is —$R^1G$.

Compounds of the formula above can include, on an aryl ring, from 1 to 4 X groups and from 0 to 4 —$YR^1G$ groups. In a preferred embodiment of the disclosed acridone compounds n is from 1 to 4. In a still more preferred embodiment of the disclosed acridone compounds n is 1, and the compounds have a —YR¹G group at only one of positions 1 to 4 on the acridone ring system. In another embodiment, the disclosed acridone compounds have the formula

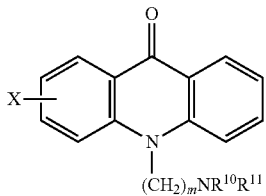

wherein m is from 2 to 10. In a further embodiment, both aryl rings bear a YR¹G moiety, examples of such compounds can be represented by the formula

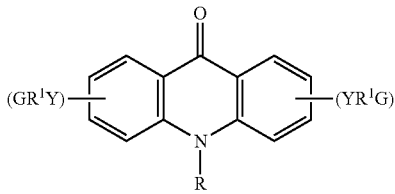

In further embodiments R can represent —R¹G, with examples of such compounds having the formula

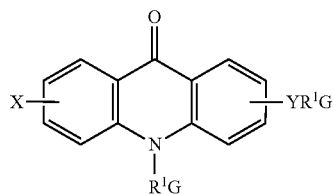

Particular embodiments of these compounds also are represented by the formula

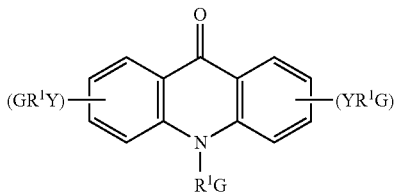

Disclosed acridones include, in some embodiments, those having R¹ be a branched alkyl group or include a cycloalkyl group. For example, R¹ optionally is substituted with a lower alkyl group, such as a methyl, ethyl, propyl or butyl group. In other examples R¹ is substituted with a hydroxy, alkoxy, lower alkyl or halo group. R¹ also can include a cyclic group, for example a cycloalkyl group.

In other embodiments, R¹ is an alkyl chain. For example, —YR¹G can represent —Y(CH₂)ₙG with n being from 2 to 10 or from 2 to 5. Particular examples of such compounds include those having the formula

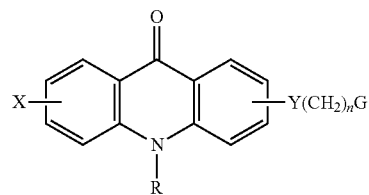

with additional examples having the formula

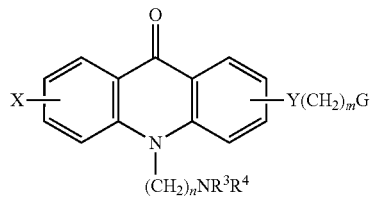

with n and m independently being from 2 to 10, such as from 2 to 5.

In particular disclosed acridone compounds having the formulas presented above, G represents —NR¹⁰R¹¹. Typically, R¹⁰ and R¹¹ independently are selected from H, lower alkyl, such as methyl, ethyl, propyl, butyl and the like; aralkyl, such as benzyl; or together form an aliphatic or aromatic ring optionally including one or more additional heteroatoms. Such cyclic groups can include, in addition to the nitrogen atom, one or more additional heteroatoms, such as an additional nitrogen, oxygen and/or sulfur atom. Specific cyclic groups represented by G include, without limitation pyrrolidino, pyridine, piperidino, morpholino, piperazino, imidazolyl, pyrazolyl or triazolyl moieties.

In certain embodiments R¹⁰ and R¹¹ are the same, such as in exemplary compounds wherein —R¹G represents —CH₂CH₂N(Et)₂. Particular examples of such N,N-diethyl substituted acridone compounds have the formula:

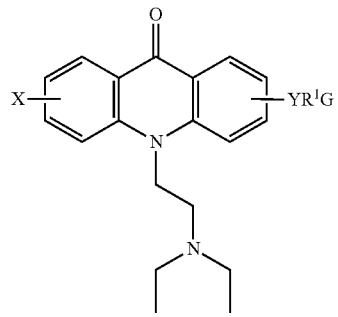

In other embodiments, R¹⁰ is H and R¹¹ represents —C(CH₃)₃. Particular examples have the formula:

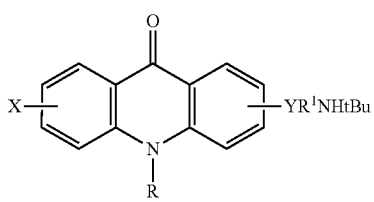

In some instances G is haloalkyl, such as bromo, chloro or fluoroalkyl. Typically, when G is a fluoroalkyl moiety, G includes at least one trifluoromethyl group. Particular examples of such haloalkyl compounds have the formula:

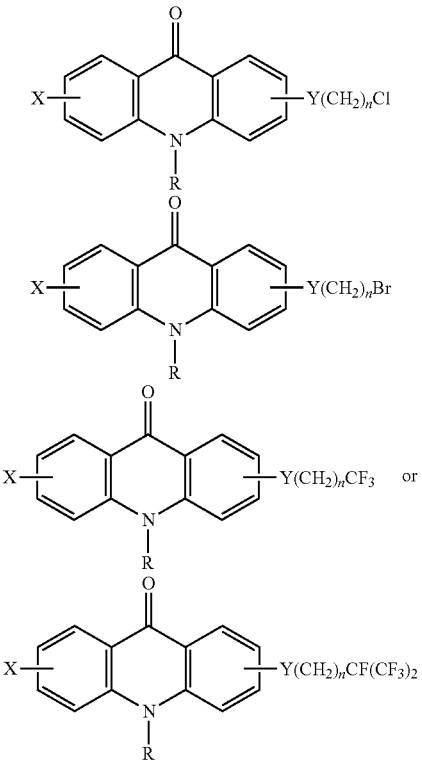

Certain disclosed acridone compounds include a halo and/or a fluoroalkyl moiety at one or more of positions 5 to 8 on the acridone ring. Particular examples of such compounds include, without limitation, the 6-chloro compounds having the formula:

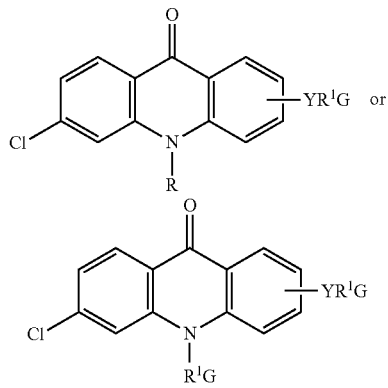

and trifluoromethyl substituted compounds of the formula:

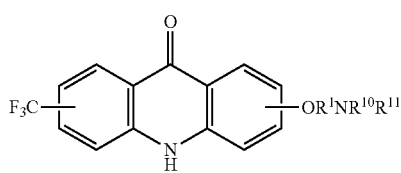

Further such compounds include a halo and/or a fluoroalkyl moiety at two or more of positions 5 to 8 on the acridone ring. Exemplary compounds can be represented by the formula:

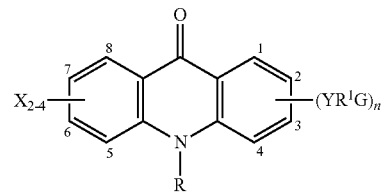

with particular embodiments including compounds of the formula:

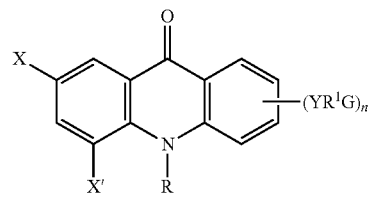

wherein X and X' independently are selected from H, halogen, haloalkyl, $OR^5$ or $—YR^1G$. In certain examples both X and X' are halogens, such as substituents.

Still other embodiments of the disclosed antiparasitic and chemosensitizing acridones are represented by the formulas:

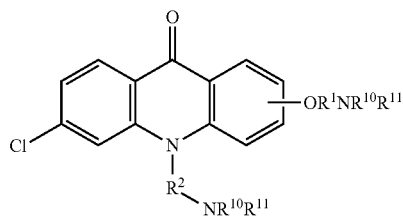

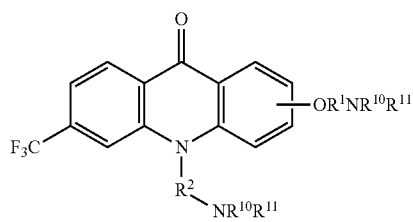

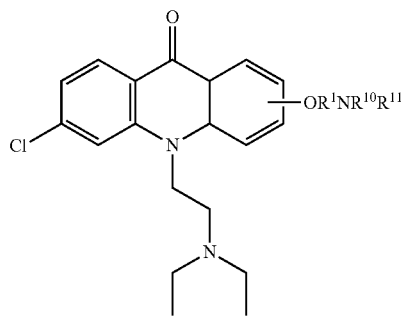

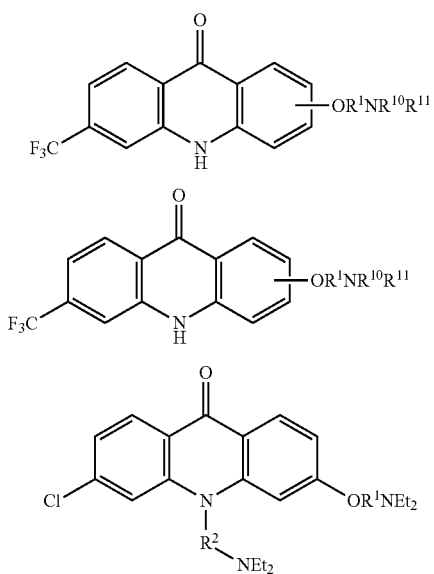
Particular examples of acridones disclosed herein include, without limitation, those of the formulas:
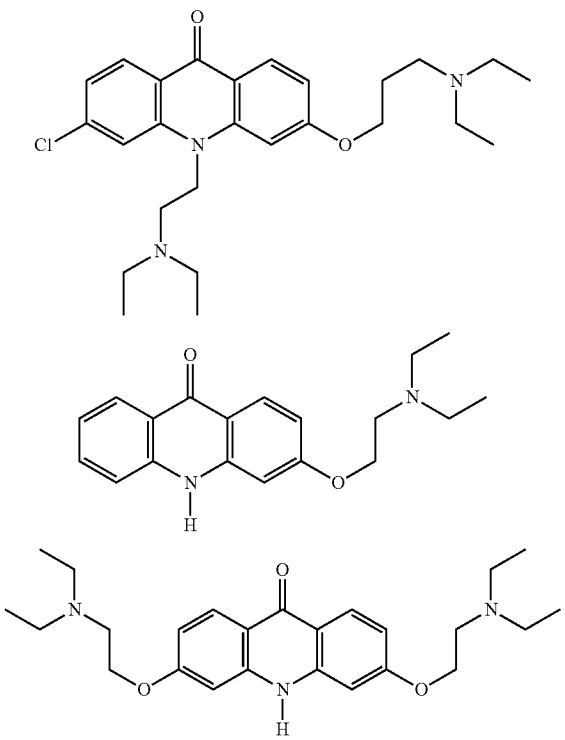
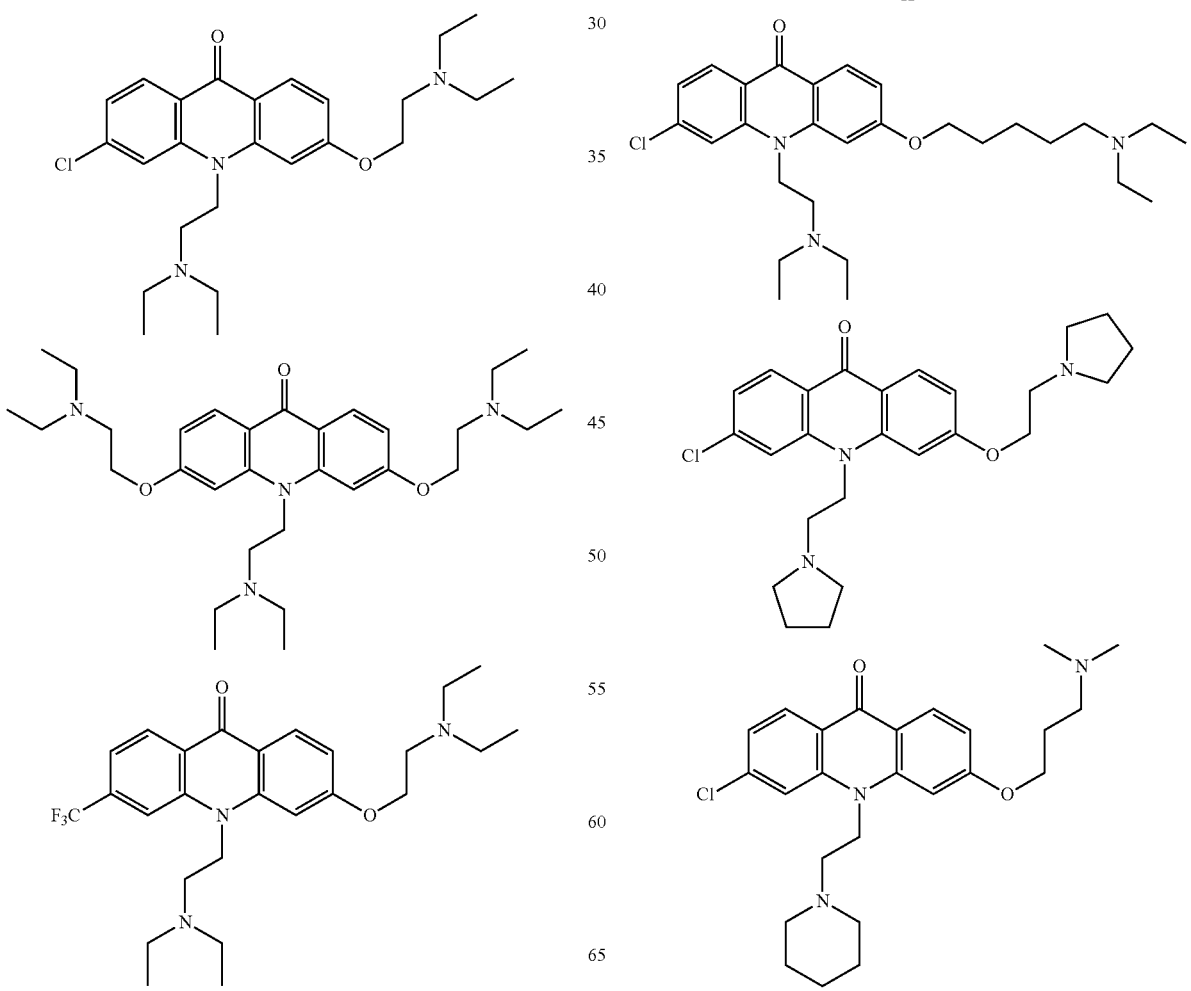

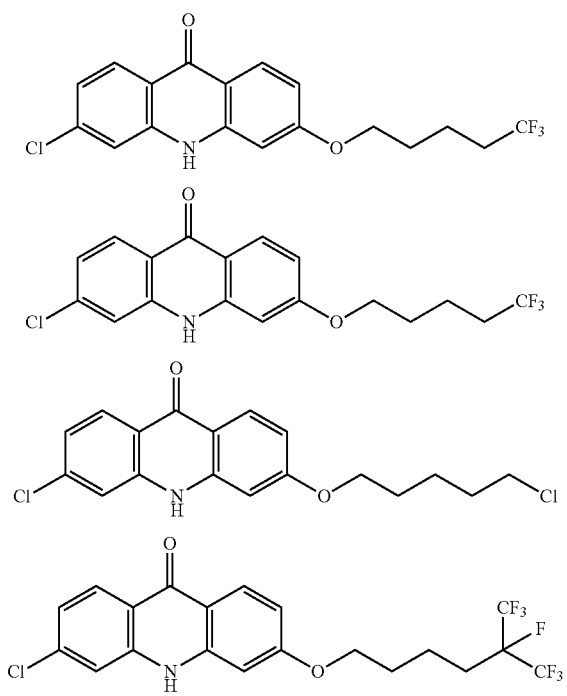
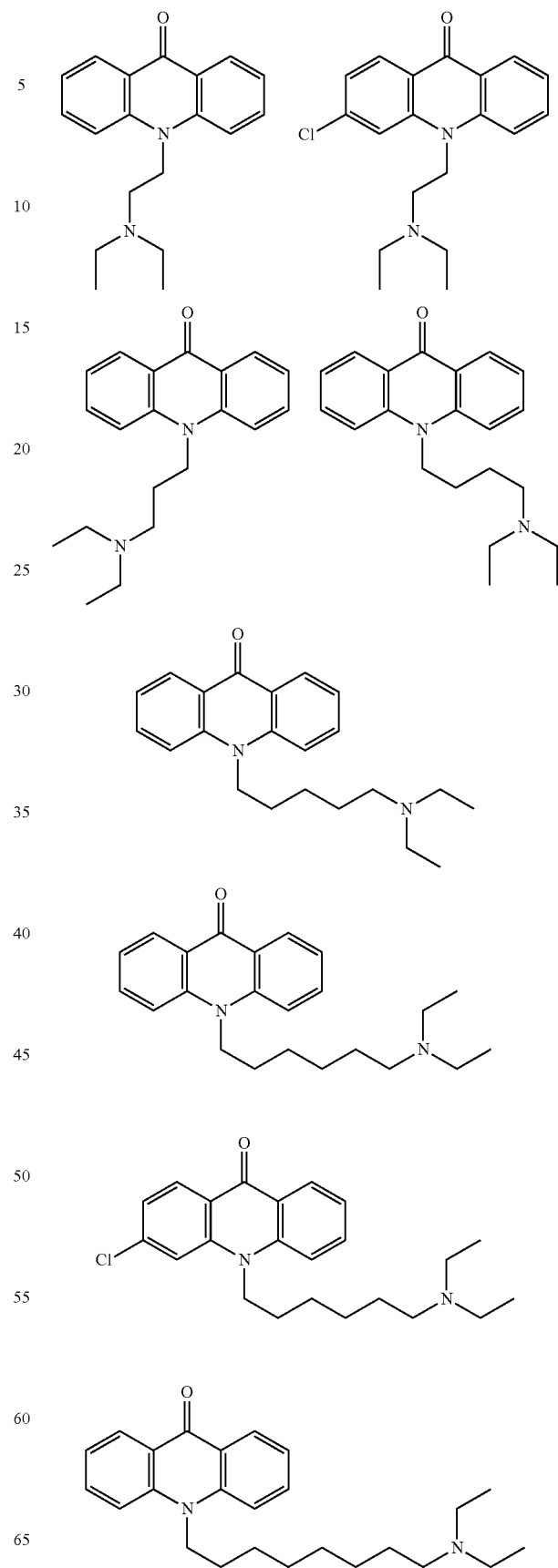

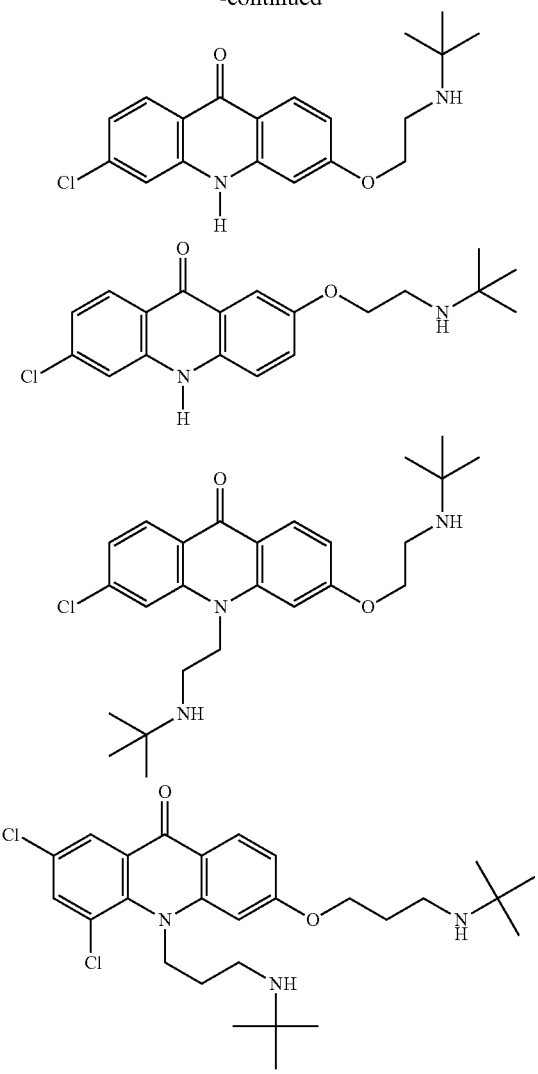

Exemplary compounds also are referred to herein by their chemical names. Such names include, without limitation, 3-(2-diethylaminoethoxy)-9-acridone; 3-(2-diethylaminoethoxy)-6-chloro-9-acridone; 2-(2-diethylaminoethoxy)-6-chloro-9-acridone; 3-(3-diethylaminopropoxy)-9-acridone; 3-(5-diethylaminopentyloxy)-6-chloro-9-acridone; 2-(2-diethylaminoethoxy)-6-chloro-10-(2-diethylaminoethyl)-9-acridone; 3-(2-diethylaminoethoxy)-6-chloro-10-(2-diethylaminoethyl)-9-acridone; and 3-(3-tert-Butylaminopropyloxy)-10-(3-tert-butylamino-propyl)-5,7-dichloro-9-acridone.

Also contemplated are pharmaceutically acceptable salts and prodrugs of the compounds described above. The term "pharmaceutically acceptable salt or prodrug" is used throughout the specification to describe any pharmaceutically acceptable form (e.g., ester, phosphate ester, salt of an amino or related group) of an acridone compound, which, upon administration to a subject, provides or produces an active compound. Pharmaceutically acceptable salts include those derived from pharmaceutically acceptable inorganic or organic bases and acids. In particular, suitable salts include those derived from alkali metals such as potassium and sodium, alkaline earth metals such as calcium and magnesium, among numerous other acids well known in the pharmaceutical art.

Particular disclosed acridone compounds possess at least one basic group (and typically plural basic groups) that can form acid-base salts with acids. Examples of basic groups include, but are not limited to, an amino group or imino group. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid.

Also disclosed are pharmaceutically acceptable prodrugs of acridone compounds. Pharmaceutically acceptable prodrugs refer to compounds that are metabolized, for example, hydrolyzed or oxidized, in the subject to form an antiparasitic or chemosensitizing compound of the present disclosure. Typical examples of prodrugs include compounds that have one or more biologically labile protecting groups on or otherwise blocking a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated (such as deesterified), phosphorylated, dephosphorylated to produce the active compound. Exemplary acridone compounds possess activity against a parasite and/or resistant cell, or are metabolized to a compound that exhibits such activity.

The term "prodrug" also is intended to include any covalently bonded carriers that release an active parent drug of the present invention in vivo when the prodrug is administered to a subject. Since prodrugs often have enhanced properties relative to the active agent pharmaceutical, such as solubility and bioavailability, the compounds disclosed herein can be delivered in prodrug form. Thus, also contemplated are prodrugs of the presently claimed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a hydroxy, amino, or sulfhydryl group functionalized with any group that is cleaved to yield the corresponding hydroxyl, free amino, or free sulfhydryl group, respectively. Examples of prodrugs include, without limitation, compounds having a hydroxy, amino and/or sulfhydryl group acylated with an acetate, formate, and/or benzoate group. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed.). Design and Application of Prodrugs, Textbook of Drug Design and Development, Chapter 5, 113 191 (1991), Bundgaard, et al., Journal of Drug Delivery Reviews, 8:1 38

(1992), Bundgaard, J. of Pharmaceutical Sciences, 77:285 et seq. (1988); and Higuchi and Stella (eds.) Prodrugs as Novel Drug Delivery Systems, American Chemical Society (1975).

Protected derivatives of the disclosed acridone compounds also are contemplated. A variety of suitable protecting groups for use with the disclosed compounds are disclosed in Greene and Wuts Protective Groups in Organic Synthesis; 3rd Ed.; John Wiley & Sons, New York (1999). Particular examples of protected derivatives include acridone compounds in which the 9-keto group is converted to an alkoxy group.

It is understood that substituents and substitution patterns of the compounds described herein can be selected by one of ordinary skill in the art to provide compounds that are chemically stable and that can be readily synthesized by techniques known in the art and further by the methods set forth in this disclosure.

The compounds described herein may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., March, *Advanced Organic Chemistry*, 4th edition, John Wiley and Sons, New York, 1992, Chapter 4).

Additionally, the structural formulas herein are intended to cover, where applicable, solvated as well as unsolvated forms of the compounds. Such solvates refer to a pharmaceutically acceptable form of a specified compound complexed with a solvent molecule, the solvate retaining the biological effectiveness of the compound. Examples of solvates include, by way of example, hydrates and compounds complexed with other solvents, such as isopropanol, ethanol, methanol, dimethyl sulfoxide, ethyl acetate and/or acetone.

III. Compositions and Methods:

Another aspect of the disclosure includes pharmaceutical compositions prepared for administration to a subject and which include a therapeutically effective amount of one or more of the currently disclosed compounds. Disclosed also are methods for administering the disclosed compounds and compositions. The therapeutically effective amount of a disclosed compound will depend on the route of administration, the type of mammal that is the subject and the physical characteristics of the subject being treated. Specific factors that can be taken into account include disease severity and stage, weight, diet and concurrent medications. The relationship of these factors to determining a therapeutically effective amount of the disclosed compounds is understood by those of ordinary skill in the art.

The compounds disclosed herein may be administered orally, topically, transdermally, parenterally, via inhalation or spray and may be administered in dosage unit formulations containing conventional non-toxic pharmaceutically acceptable carriers, adjuvants and vehicles.

Typically, oral administration or administration intravenously, such as via injection is preferred. However the particular mode of administration employed may be dependent upon the particular disease, condition of patient, toxicity of compound and other factors as will be recognized by a person of ordinary skill in the art.

Pharmaceutical compositions for administration to a subject can include carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. Pharmaceutical formulations can include additional components, such as carriers. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

In certain embodiments the compounds used in the method are provided are polymorphous. As such, the compounds can be provided in one or more physical form, such as different crystal forms, crystalline, liquid crystalline or non-crystalline (amorphous) forms.

Also disclosed herein is a method of inhibiting the growth of a microbial pathogen, such as a parasite, particularly a protozoan parasite, such as those responsible for diseases such as malaria, trypanosomiasis, Chagas' disease, leishmaniasis, giardiasis, and amoebiasis. Also discloses are methods for the inhibition of diseases caused by *Toxoplasma* sp., *Mycobacterium* sp., and *Pneumocystis* sp. The method comprises providing an effective amount of an acridone compound to inhibit pathogen growth in vivo or in vitro.

In one aspect, the method can be used to treat a subject having a microbial infection. The method comprises administering to the subject a therapeutically effective amount of a disclosed acridone compound, such as at least about 0.005 mg/kg. In certain embodiments, the acridone is administered at a dose of at least about 0.02 mg/kg. Typically, no more than about 250 mg/kg of the agent is administered, and more typically less than about 50 mg/kg, and even more typically less than about 10 mg/kg such as about 5 mg/kg or about 0.2 mg/kg. Hence in certain embodiments the dosage range is about 0.005 to about 10 mg/kg, or about 0.02 to about 5 mg/kg, or about 0.2 to about 5 mg/kg, such as from about 1 to about 5 mg/kg.

Certain disclosed compounds inhibit the aggregation of heme. A number of pathogens, including trypanosomes, such as *Plasmodium*, a causative agent of malaria, degrade hemoglobin to obtain amino acids, and in so doing liberate toxic heme. To avoid the toxic effects of the liberated heme, these pathogens have evolved a mechanism for "aggregation" of heme units to form hemozoin. Thus, without limitation to theory, the disclosed acridone inhibitors of heme aggregation may exert their antiparasitic effect by blocking heme aggregation and preventing these organisms from gaining access to the host's supply of heme iron, or by causing a build-up of toxic levels of heme in the organism.

The disclosed acridone compounds are particularly effective when used with one or more other agents or therapies useful in the treatment of resistant disorders, such as disorders caused by multidrug resistant cells. For example, one or more disclosed acridones can be administered in combination with effective doses of other medicinal and pharmaceutical agents, or in combination other non-medicinal therapies, such as hormone or radiation therapy. The term "administration in combination with" refers to both concurrent and sequential administration of the active agents.

In one embodiment the disclosed acridone compounds are used in a method of enhancing the intracellular accumulation of a drug in multidrug resistant cells wherein the accumulation depends upon inhibiting transport by the multidrug resistance transport system involving P-glycoprotein. In such methods, the compounds of the present invention are coadministered with the drug.

The administration may be in vitro or in vivo. In some embodiments, the enhancement of accumulation of the drug in multidrug resistant cells is in vivo. In particular embodiments, one or more disclosed acridone compound is administered to a cancer patient to treat a tumor that has become multidrug resistant in the course of therapy. Typically, in such embodiments, chemotherapeutic agents are administered with the compounds of the present invention. The coadministration is designed to enhance accumulation of the agent following reversal of the multidrug resistant phenotype by interaction of the compounds of the present invention with the multidrug resistance transport system. Thus, the coadministration is designed to cause the chemotherapeutic agent to accumulate in amounts effective for cytotoxicity, whereas when the agent is administered alone, accumulation in effective amounts does not occur. This coadministration regimen can be applied to any cell which exhibits the multidrug resistance phenotype, for example, as a result of overexpression of the multidrug resistance protein, e.g., P-glycoprotein.

In certain cases, the disclosed acridones in combination with at least one other therapeutic agent exhibit a synergistic effect. Synergy is observed when the agents administered have a greater than additive effect when administered in combination. In other embodiments the disclosed acridones exhibit synergy with one or more antitumor, antiviral, antiparasitic (such as anti-trypanosomal, such as antimalarial) or antibiotic agent. Thus, the disclosed acridones are used in combination to treat viral infections, such as retroviral, for example HIV infections; neoplasms, particularly malignant neoplasms; bacterial infections, such as S. aureus, S. epidermidis, S. pneumoniae, E. faecalis, E. faecium, and drug resistant Gram positive cocci, such as methicillin-resistant staphylococci and vancomycin-resistant enterococci; and parasitic infections, such as trypanosomal infections, for example malaria, schistosomiasis, toxoplasmosis, and leishmaniasis. In particular embodiments, the acridone compounds exhibit, in combination with a second therapeutic agent a fixed-ratio concentration synergism of less than about 1, such less than about 0.8, particularly less than about 0.5.

In particular the disclosed acridones are effective against malaria and/or Plasmodium sp. parasitemia either alone or in combination with one or more additional antimalarial agents or therapies. In some examples, the one or more antimalarial agents or therapies for use in combination with the disclosed acridones include artesunate and mefloquine (either individually or in an artesunate-mefloquine combination), or sulfadoxine and pyrimethamine (either individually or in a sulfadoxine-pyrimethamine combination (commercially available as FANDISAR)). In particular examples, the one or more other antimalarial agents or therapies have at least one different mode of action than is proposed for a disclosed acridone; thus, for instance, a combination agent or therapy may target mitochondria and/or dihydrofolate reductase.

In one embodiment the disclosed acridones can be used either alone or in combination with another drug to effect a curative treatment regiment. As used herein a curative dose refers the dose at which parasitemia is cleared for 28 days. Typically, the curative dose is administered over several days, such as for 1 to 10 days, such as over 1 to 7 days, such as from 2 to 5 days, for example over 3 days. The curative dose can be administered once to several times daily, and typically is given in a once, twice or three times daily dosage regimen.

For malaria prevention, a typical dosing schedule could be, for example, about 2.0 to about 1000 mg/kg weekly beginning about 1 to about 2 weeks prior to malaria exposure taken up until about 1 to about 2 weeks post-exposure. The prophylactic dose also can be given in a once daily to several times daily dosage regimen.

In certain embodiments the disclosed acridones can be used as chemosensitizing agents to restore the clinical efficacy of an antimalarial drug to which a parasite strain has required resistance. For example, in certain examples the efficacy of a drug can be restored by administration of a disclosed acridone compound. In particular, the efficacy of quinoline based antimalarials, such as quinine, chloroquine and quinidine can be restored against resistant parasites by coadministration with a disclosed acridone.

Although the acridones disclosed herein act as reversal agents, in one embodiment, the disclosed acridones are used to treat a parasitic infection, such as malaria, in combination with a sensitizing or reversal agent. In particular, reversal agents are suitable for coadministration with the disclosed acridone compounds. By way of example, reversal agents suitable for coadministration with the disclosed acridones include, without limitation, amitriptyline, amlodipine, azatadine, chlorpheniramine, citalopram, cyclosporine, cyproheptadine, cyproheptadine, desipramine, diethyl-{3-[3-(4-methoxy-benzylidene)-pyrrolidin-1-yl]-propyl}-amine, erythromycin, fantofarone, fluoxetine, haloperidol, icajine, imipramine, isoretuline, ivermectin, ketotefin, ketotifen, nomifensine, NP30: $C_9H_{19}$-Phenyl-(O—$CH_2CH_2$)$_{30}$OH, oxaprotiline, probenecid, progesterone, promethazine, strychnobrasiline, BG958, trifluoperazine, verapamil, or WR 268954. Other useful combinations include combination with CQ, desethyl-CQ, quinine, mefloquine or amodiaquine against multidrug resistant P. falciparum Dd2.

As noted above, in embodiments of combination therapy disclosed herein, a disclosed acridone is used to sensitize a multidrug resistant neoplasm to a chemotherapeutic agent. In one embodiment, the chemotherapeutic agent is an agent of use in treating neoplasms such as solid tumors. Examples of such chemotherapeutic agents can that can be used in combination with a disclosed acridone include microtubule binding agents, DNA intercalators or cross-linkers, DNA synthesis inhibitors, DNA and/or RNA transcription inhibitors, antibodies, enzymes, enzyme inhibitors, gene regulators, and/or angiogenesis inhibitors. One of skill in the art can readily identify additional chemotherapeutic agents of use (e.g., see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer L, Berkery R (eds.): Oncology Pocket Guide to Chemotherapy, 2nd ed. St. Louis, Mosby-Year Book, 1995; Fischer D S, Knobf M F, Durivage H J (eds.): The Cancer Chemotherapy Handbook, 4th ed. St. Louis, Mosby-Year Book, 1993).

In addition to treating diseases such as malaria, the compounds described can be used to treat other parasitic diseases such as toxoplasmosis. Toxoplasmosis is caused by a sporozoan parasite of the Apicomplexa called the *Toxoplasma gondii*. It is a common tissue parasite of humans and animals.

Approximately 1 billion people worldwide are sero-positive for *T. gondii*, including roughly half of the U.S. population. Humans are merely incidental hosts for the organism, i.e., hosts to the asexual cycle only. Most of the infections appear to be asymptomatic (90%), however toxoplasmosis poses a serious health risk for immuno-compromised individuals, such as organ transplant recipients, cancer and AIDS patients, and the unborn children of infected mothers. Congenital toxoplasmosis occurs in about 1 in 1,000 live births with effects ranging from asymptomatic to stillbirth, but more commonly retinochoroiditis, cerebral calcification, psychomotor deficit, or mental retardation, and severe brain damage.

*T. gondii* is an obligate intracellular protozoon. There are three infectious stages in the developmental cycle of *T. gondii*, the trophozoite (tachyzoite), the bradyzoites (tissue cyst forms), and the sporozoites that are found in oocysts. The tachyzoite presents as an active developmental stage in which the parasites undergo multiplication within a host cell. In this stage the parasite has the shape of a small crescent, roughly 2 by 6 μm, with a pointed anterior end and a rounded posterior end. Accumulation of numerous *T. gondii* within a single host cell has been termed as the pseudocyst form. The cyst form of *T. gondii* is essentially a resting, non-proliferating stage of the parasite, and a tough membrane protects the organisms. Cysts range in size from 30 to 100 microns, and predominate in chronic infections and accumulate in brain, heart muscle, and the diaphragm of the host. Each cyst contains many hundreds or thousands of organisms and although sizeable in nature and somewhat damaging to host tissues, it is interesting to note that there is rarely local immune reaction to the presence of the invading organisms or their dwellings. These cysts can reside in the human host for life.

The cat is the definitive host (i.e., host to the parasite sexual cycle) for *T. gondii* and is needed to complete its life cycle. Ingestion of tissue cysts in an intermediate host, such as a mouse or a rat, leads to infection of the cat. The organisms penetrate epithelial cells of the small intestine of the cat and initiate the development of numerous generations of *T. gondii*. After a process of asexual development, the sexual cycle starts about 2 days after tissue cysts have been ingested by the cat, yielding oocysts which are passed in the feces and picked up by animals from contaminated water or by ingestion of infected meat.

Recent scientific experiments have shown a link between infectious agents and psychotic diseases. For example, acute infection of human beings with *T. gondii* can produce symptoms similar to schizophrenia. See, Toney and Yolken, *Toxoplasma gondii* and Schizophrenia, *Emerg. Infect. Dis.* 9(11), 1375-1380 (2003) and *Schizophr Bull.* 33(3), 727-728 (2007), both references incorporated herein, in their entirety, by reference. For example, mothers having antibodies to *T. gondii* late in pregnancy had an increased risk of giving birth to offspring who later developed a schizophrenia spectrum disorder. Other studies have found that newborns that are sero-positive for antibodies to *T. gondii* have an increased risk of later being diagnosed with schizophrenia. Schizophrenia is a debilitating disease of the mind and has been described as one of the worst diseases to affect mankind and one of the most expensive diseases to treat. It affects about 1% of the population of the United States.

In humans, toxoplasmosis is generally treated by a combination of sulfonamides and pyrimethamine. Although these drugs are helpful in management of the acute stage of disease, they usually do not eradicate infection and treatment failure rates of 20 to 50% have been reported. Atovaquone, a second line therapeutic for treatment of toxoplasmosis, is the only drug known to have some activity against the dormant cyst stage; it is believed to target the parasite respiratory pathway at the cytochrome $bc_1$ complex. Efficacy of atovaquone is limited by its variable intestinal absorption.

The compounds described herein may be used as an adjunct to, or replacement of, drugs such as atovaquone. Treatment of parasitic infections such as toxoplasmosis by using the compounds and methods described herein, is within the scope of this disclosure. Another embodiment is the treatment of psychiatric diseases and disorders by administration of the compounds described herein. These compounds may be used to treat not only the disease or disorder but may also be used to treat the symptoms and effects of the disease or disorder. For example, a subject afflicted by schizophrenia may exhibit symptoms such as delusions, ahedonia, and avolition.

EXAMPLES

The following examples are provided to illustrate certain particular features and/or embodiments. These examples should not be construed to limit the invention to the particular features or embodiments described.

Example 1

This example describes the in vitro inhibition of heme aggregation by xanthone 2,3,4,5,6-pentahydroxyxanthone. Conditions: 25 mM Phosphate buffer, pH 5.2, 1 hour incubation at 37° C. Further details of this assay are described by Ignatushchenko et al. in Xanthones as antimalarial agents; studies of a possible mode of action. *FEBS Lett.* 409, 67-73 (1997). With reference to FIG. 1, panel A, the left tube contains heme alone; the center tube contains heme with the xanthone; and the right: tube includes heme with chloroquine.

With continued reference to FIG. 1, panel B illustrates the spectrophotometric titration curve of the heme:3,6-bis-ε-(N, N-diethylamino)-amyloxy xanthone (C5) complex. The apparent binding constant was derived from the best fit (solid line) of a 1:1 (heme dimer:C5) association model. Panel C includes images from confocal fluorescence microscopy of C5 and LysoTracker Red accumulation in a *P. falciparum* infected erythrocyte. Panels A and B show the fluorescence localization of C5 and LysoTracker Red, respectively. Panel C shows the brightfield transmission image of the infected cell overlaid with the image from Panel A. Panel D shows the merged image demonstrating co-localization of C5 and LysoTracker Red.

Example 2

This example illustrates the ability of disclosed antimalarial acridones, such as 10-(ω-(N,N-diethylamino-alkyl)acridones to enhance CQ potency against MDR *P. falciparum* strains W2 and Dd2. The response modification index (RMI) was used to represent the IC50 of CQ in the presence of a fixed concentration of the test acridones in comparison to CQ alone (RMI=IC50 of CQ with acridone/IC50 of CQ alone). The results are summarized in Table 1. An RMI of 1.0 indicates no change in IC50 upon addition of a resistance reversal agent, >1.0 indicates antagonism, and <1.0 indicates chemosensitization and possible synergism.

TABLE 1
In vitro chemosensitization to chloroquine in the presence of 5 μM acridone derivatives and selected known chemo sensitizers.
| Drug combination | Chemosensitizer Structure | W2 IC$_{50}$$^a$(nM) | W2 RMI$^b$ | Dd2 IC$_{50}$$^a$(nM) | Dd2 RMI$^b$ | Calc'd pK$_a$$^c$ |
|---|---|---|---|---|---|---|
| Chloroquine (CQ) alone | 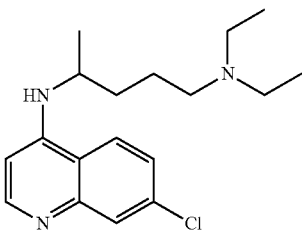 [SMILES: CCN(CC)CCCC(C)Nc1ccnc2cc(Cl)ccc12] | 290.0 | — | 100.2 | — | 10.3 6.3 |
| CQ + A2 | 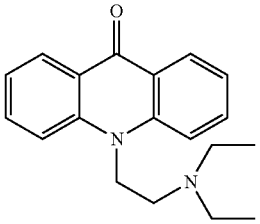 [SMILES: CCN(CC)CCn1c2ccccc2c(=O)c2ccccc21] | 259.3 | 0.88 | 80.9 | 0.76 | 9.81 |
| CQ + A3 | 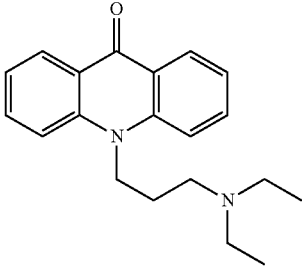 [SMILES: CCN(CC)CCCn1c2ccccc2c(=O)c2ccccc21] | 60.9 | 0.21 | 33.4 | 0.31 | 10.28 |
| CQ + A4 | 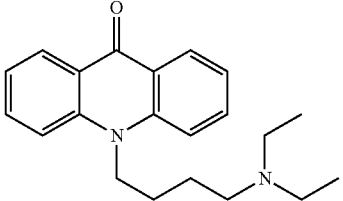 [SMILES: CCN(CC)CCCCn1c2ccccc2c(=O)c2ccccc21] | 35.3 | 0.12 | 12.0 | 0.11 | 10.46 |
| CQ + A5 | 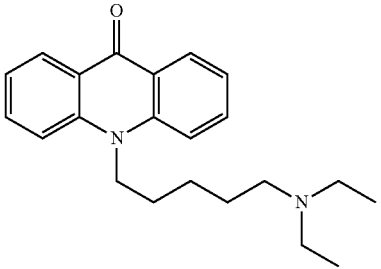 [SMILES: CCN(CC)CCCCCn1c2ccccc2c(=O)c2ccccc21] | 30.5 | 0.10 | 11.3 | 0.11 | 10.53 |
| CQ + A6 | 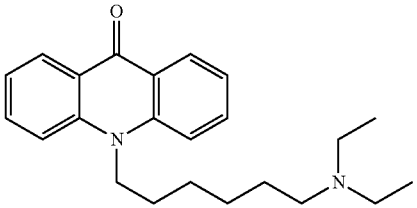 [SMILES: CCN(CC)CCCCCCn1c2ccccc2c(=O)c2ccccc21] | 17.8 | 0.06 | 8.1 | 0.08 | 10.56 |

TABLE 1-continued

In vitro chemosensitization to chloroquine in the presence of 5 µM acridone derivatives and selected known chemo sensitizers.

| Drug combination | Chemosensitizer Structure | W2 IC$_{50}$$^a$(nM) | W2 RMI$^b$ | Dd2 IC$_{50}$$^a$(nM) | Dd2 RMI$^b$ | Calc'd pK$_a$$^c$ |
|---|---|---|---|---|---|---|
| CQ + A8 | | 39.5 | 0.14 | 15.5 | 0.16 | 10.65 |
| CQ + A6-Cl | | 550.4 | 1.87 | 176.9 | 1.66 | — |
| CQ + verapamil | | 51.8 | 0.18 | 21.5 | 0.2 | 8.6 |
| CQ + desipramine | | 29.0 | 0.10 | 10.0 | 0.10 | 10.4 |
| CQ + chlorpheniramine | | 58.0 | 0.20 | 11.0 | 0.11 | 10.2 |

$^a$IC$_{50}$ of CQ in combination with 5 µM of selected drug.
$^b$RMI = IC$_{50}$ of CQ in combination/IC$_{50}$ of CQ alone.
$^c$pK$_a$ calculated with ChemSketch I-Lab Acridones A2, A3, A4, A5, A6, A8, with a tertiary amine at the end of the carbon chain attached at the N-10 position, increased, in some cases dramatically, the sensitivity W2 and Dd2 to CQ. In the presence of 5 µM A6, the IC$_{50}$ of CQ was potentiated by over 90-fold in both of the MDR strains to a level (17.8 nM, W2; 8.1 nM, Dd2) approximately equivalent to that observed for the CQ-sensitive strain D6 (15 nM). Acridone congeners A3 to A6 were efficacious chemosensitizers, and disclosed acridone compounds A4 to A6 exhibited comparable or superior chemosensitization, to the known agents verapamil, desipramine, and chlorpheniramine.

Example 3

This example describes the screening of disclosed antimalarial acridones against the CQ-sensitive D6 strain and the MDR Dd2 strain of *P. falciparum* for in vitro antimalarial activity. The results of the screening of exemplary acridones are recorded in Table 2.

Notably, the screened compounds were equally potent against D6 and Dd2. For most of the compounds, including T2 and T3.5, there was no evidence of cytotoxicity at the highest tested concentration (25 µM), and less cytotoxicity than CQ. All of the compounds illustrated in Table 3 are weak bases (pK$_a$ 9.5-10.5), favoring accumulation of their charged form inside the acidic parasite digestive vacuole, particularly in the case of the dibasic compounds. It is also noteworthy that the c Log P values are <5, indicating adequate aqueous solubility for realistic drug delivery.

TABLE 2

In vitro assessment of antimalarial potency vs. sensitive & multidrug resistant strains of *P. falciparum*.

| Drug Name | Structure | IC$_{50}$$^a$, nM | | IC$_{50}$$^b$, nM | IVTI$^c$ | pK$_a$$^e$ |
|---|---|---|---|---|---|---|
| | | D6 | Dd2 | MSLCs | | |
| 3-(2-diethylaminoethoxy)-9-acridone (T1) | 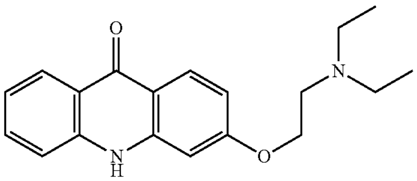 [SMILES: CCN(CC)CCOc1ccc2c(=O)c3ccccc3[nH]c2c1] | 167 | 159 | >25,000 | >150 | 9.5 |
| 3-(2-diethylaminoethoxy)--6-chloro-9-acridone (T2) | 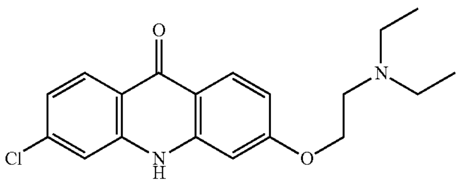 [SMILES: CCN(CC)CCOc1ccc2c(=O)c3ccc(Cl)cc3[nH]c2c1] | 18 | 17 | >25,000 | >1389 | 9.5 |
| 3-(2-diethylaminoethoxy)-6-chloro-xanthone (TX2) | 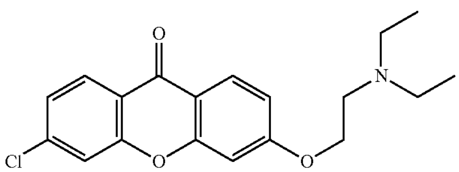 [SMILES: CCN(CC)CCOc1ccc2c(=O)c3ccc(Cl)cc3oc2c1] | >2,500 | >2,500 | >25,000 | NA | 9.5 |
| 2-(2-diethylaminoethoxy)--6-chloro-9-acridone (T2.2) | 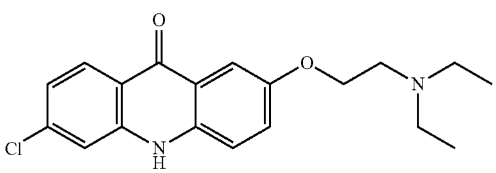 [SMILES: CCN(CC)CCOc1ccc2[nH]c3cc(Cl)ccc3c(=O)c2c1] | 106 | 123 | >25,000 | >235 | 9.5 |
| 3-(3-diethylaminopropoxy)-9-acridone (T3) | 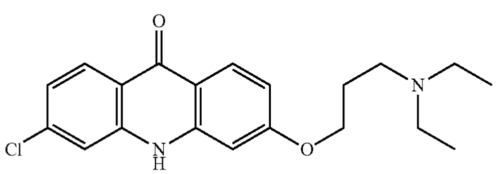 [SMILES: CCN(CC)CCCOc1ccc2c(=O)c3ccc(Cl)cc3[nH]c2c1] | 60 | 60 | >25,000 | >417 | 10.1 |
| 3-(5-diethylaminopentyloxy)-chloro-9-acridone (T5) | 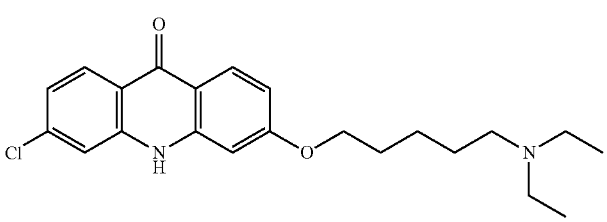 [SMILES: CCN(CC)CCCCCOc1ccc2c(=O)c3ccc(Cl)cc3[nH]c2c1] | 84 | 125 | 10,000 | 119 | 10.5 |
| 2-(2-diethylaminoethoxy)--6-chloro-10-(2-diethyl-aminoethyl)-9-acridone (T2.2.5) | 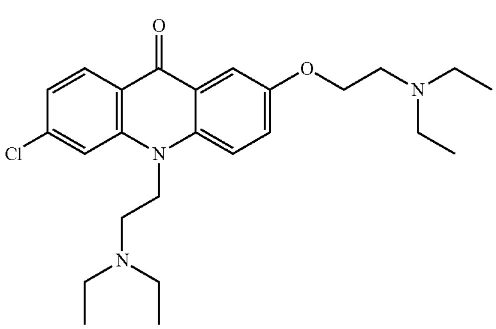 [SMILES: CCN(CC)CCOc1ccc2c(c1)c(=O)c1ccc(Cl)cc1n2CCN(CC)CC] | 79 | 86 | >25,000 | >316 | 9.8 9.5 |

TABLE 2-continued

In vitro assessment of antimalarial potency vs. sensitive & multidrug resistant strains of P. falciparum.

| Drug Name | Structure | $IC_{50}^{a}$, nM | | $IC_{50}^{b}$, nM | $IVTI^{c}$ | $pK_{a}^{e}$ |
|---|---|---|---|---|---|---|
| | | D6 | Dd2 | MSLCs | | |
| 3-(2-diethylaminoethoxy)--6-chloro-10-(2-diethyl-aminoethyl)-9-acridone (T3.5) | [structure] | 50 | 58 | >25,000 | >500 | 9.7 9.5 |
| Chloroquine | [structure] | 6.8 | 132 | 1,300 | 191 | 10.3 6.3 |

[a] The SYBR Green MSF assay was used for $IC_{50}$ determinations; the values are the average of 4 independent experiments.
[b] MSLCs = Murine splenic lymphocytes. Cytotoxicity was determined by the Alamar Blue assay.
[c] IVTI = ratio of cytotoxicity $IC_{50}$ (vs. MSLCs) to antimalarial $IC_{50}$ against D6.
[e] $pK_{a}$ values were calculated with ChemSketch I-Lab As shown in Table 3 and Table 4, selected soluble acridone derivatives were screened for antimalarial activity against the CQ-sensitive D6 and the MDR Dd2 strains of P. falciparum.

TABLE 3

In vitro intrinsic antimalarial activity, cytotoxicity, heme-binding affinity, and physical properties of selected acridones without N-10 substitution.

| Drug | Structure | $IC_{50}$* (nM) P. falciparum | | $IC_{50}$ (nM)[a] | $cLogP^{b}$ | Heme-binding $K_{a}^{c}$ ($10^{4}M^{-1}$) |
|---|---|---|---|---|---|---|
| | | D6* | Dd2* | MSLCs | | |
| T1 | [structure] | 167 | 159 | >25,000 | 3.2 | TBD |
| T2 | [structure] | 26 | 33 | >25,000 | 3.8 | 4.3 |

TABLE 3-continued
In vitro intrinsic antimalarial activity, cytotoxicity, heme-binding affinity, and physical properties of selected acridones without N-10 substitution.
| Drug | Structure | IC$_{50}$* (nM) P. falciparum D6* | IC$_{50}$* (nM) P. falciparum Dd2* | IC$_{50}$ (nM)$^a$ MSLCs | cLogP$^b$ | Heme-binding K$_a{}^c$ (10$^4$M$^{-1}$) |
|---|---|---|---|---|---|---|
| T2.1 | 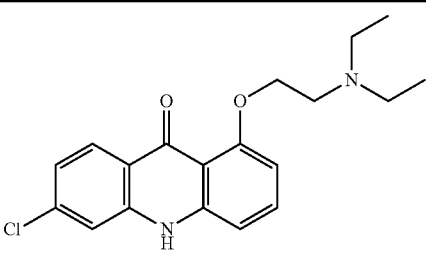 | 240 | 420 | >25,000 | 3.8 | TBD |
| T2.2 | 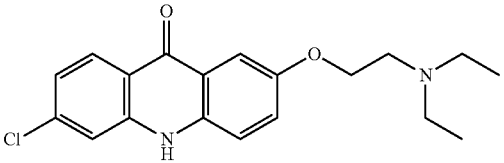 [SMILES: CCN(CC)CCOc1ccc2[nH]c3cc(Cl)ccc3c(=O)c2c1] | 70 | 126 | >25,000 | 3.8 | 5.4 |
| T3 | 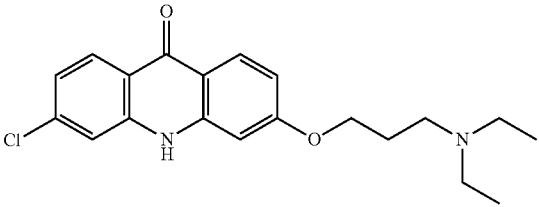 [SMILES: CCN(CC)CCCOc1ccc2c(=O)c3ccc(Cl)cc3[nH]c2c1] | 104 | 109 | >25,000 | 3.9 | TBD |
| T4 | 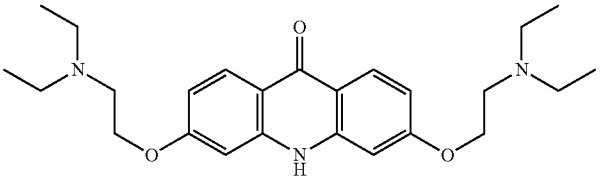 [SMILES: CCN(CC)CCOc1ccc2c(=O)c3ccc(OCCN(CC)CC)cc3[nH]c2c1] | 398 | 759 | >25,000 | 3.8 | TBD |
| T5 | 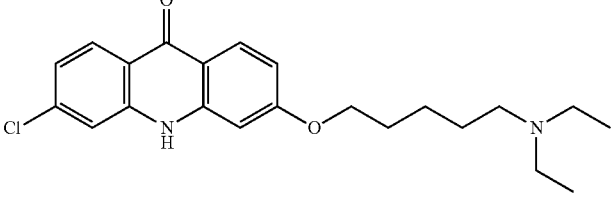 | 76 | 61 | >25,000 | 4.7 | TBD |
| T6 | 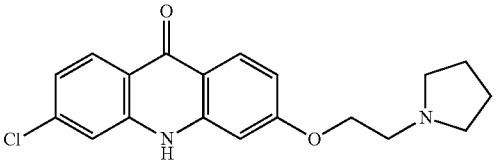 [SMILES: O=c1c2ccc(Cl)cc2[nH]c2cc(OCCN3CCCC3)ccc12] | 270 | 390 | TBD | 3.4 | TBD |
| T7 | 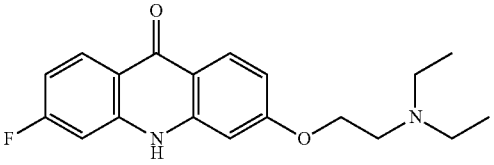 [SMILES: CCN(CC)CCOc1ccc2c(=O)c3ccc(F)cc3[nH]c2c1] | 90 | 49 | TBD | 3.2 | TBD |

TABLE 3-continued

In vitro intrinsic antimalarial activity, cytotoxicity, heme-binding affinity, and physical properties of selected acridones without N-10 substitution.

| Drug | Structure | $IC_{50}$* (nM) P. falciparum | | $IC_{50}$ (nM)$^a$ | cLogP$^b$ | Heme-binding $K_a{}^c$ ($10^4 M^{-1}$) |
|---|---|---|---|---|---|---|
| | | D6* | Dd2* | MSLCs | | |
| T8 | 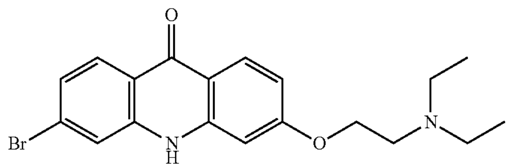 [SMILES: CCN(CC)CCOc1ccc2c(=O)c3ccc(Br)cc3[nH]c2c1] | 12 | 19 | TBD | 3.9 | TBD |
| T9 | 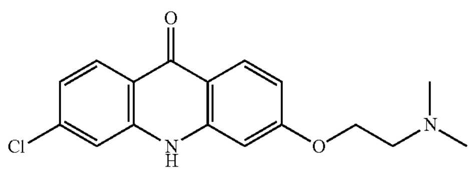 [SMILES: CN(C)CCOc1ccc2c(=O)c3ccc(Cl)cc3[nH]c2c1] | 56 | 63 | TBD | 2.7 | TBD |
| TX2 | 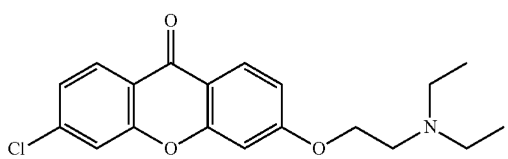 [SMILES: CCN(CC)CCOc1ccc2c(=O)c3ccc(Cl)cc3oc2c1] | >2,500 | >2,500 | >25,000 | 3.9 | TBD |
| CQ† | 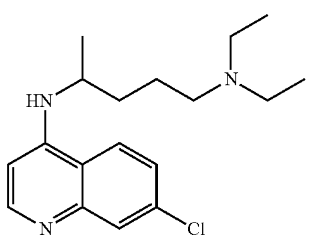 [SMILES: CCN(CC)CCCC(C)Nc1ccnc2cc(Cl)ccc12] | 8.4 | 124 | 1,300 | 3.1 | 5.5 |
| ATV† | 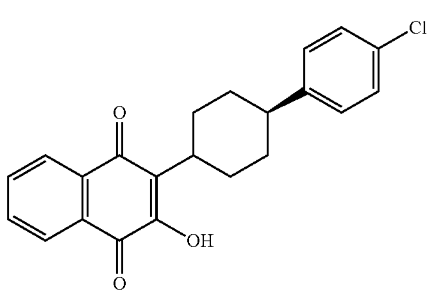 | 0.1 | 0.1 | >25,000 | 3.7 | — |

TBD: to be determined

*All $IC_{50}$ were assessed by MSF assay; D6: CQ sensitive; Dd2: MDR, Old World genetic background; See text for details.

$^a$MSLCs = murine splenic lymphocytes. Cytotoxicity was determined by the Alamar Blue assay.

$^b$LogP values were calculated with ChemDraw Ultra 8.0 software.

TABLE 4

In vitro antimalarial activity, cytotoxicity, and heme-binding affinity, of selected acridones.

| DRUG | Structure | IC$_{50}$ (nM) P. falciparum D6* | Dd2* | IC$_{50}$ (nM)$^a$ MSLCs | Heme-binding K$_a^b$ (10$^4$M$^{-1}$) |
|---|---|---|---|---|---|
| T3.5 | 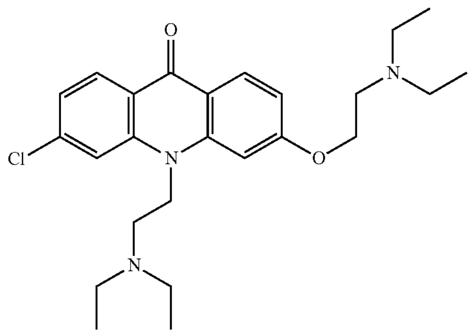 [SMILES: CCN(CC)CCOc1ccc2c(=O)c3ccc(Cl)cc3n(CCN(CC)CC)c2c1] | 44 | 77 | >25,000 | 7.1 |
| T2.1.5 | 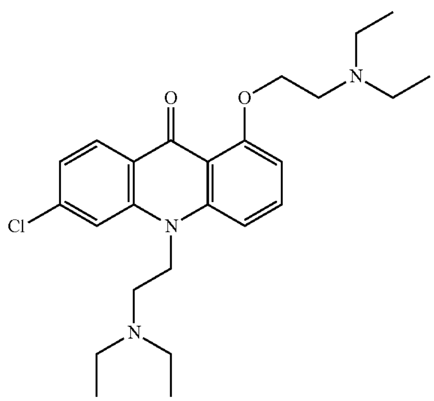 [SMILES: CCN(CC)CCOc1cccc2c1c(=O)c1ccc(Cl)cc1n2CCN(CC)CC] | 33 | 84 | >25,000 | TBD |
| T2.2.5 | 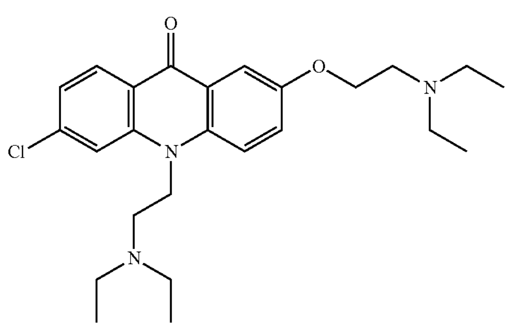 [SMILES: CCN(CC)CCOc1ccc2c(c1)c(=O)c1ccc(Cl)cc1n2CCN(CC)CC] | 56 | 133 | >25,000 | TBD |
| T4.5 | 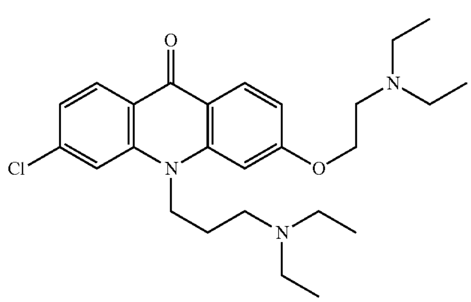 [SMILES: CCN(CC)CCCn1c2cc(Cl)ccc2c(=O)c2ccc(OCCN(CC)CC)cc21] | 47 | 100 | >25,000 | TBD |

TABLE 4-continued

In vitro antimalarial activity, cytotoxicity, and heme-binding affinity, of selected acridones.

| DRUG | Structure | IC$_{50}$ (nM) P. falciparum D6* | Dd2* | IC$_{50}$ (nM)$^a$ MSLCs | Heme-binding K$_a^b$ (10$^4$M$^{-1}$) |
|---|---|---|---|---|---|
| T5.5 | 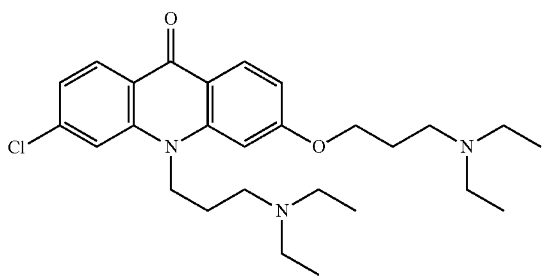 [SMILES: CCN(CC)CCCOc1ccc2c(=O)c3ccc(Cl)cc3n(CCCN(CC)CC)c2c1] | 76 | 109 | 8,900 | TBD |
| T7.5 | 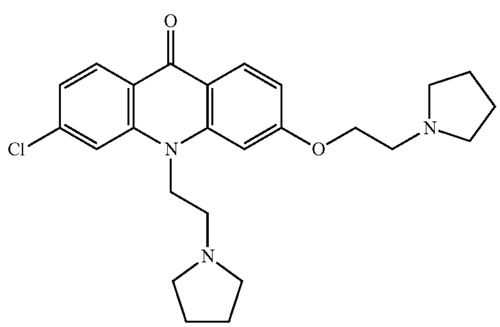 [SMILES: O=c1c2ccc(Cl)cc2n(CCN2CCCC2)c2cc(OCCN3CCCC3)ccc12] | 17 | 20 | TBD | 4.3 |
| T8.5 | 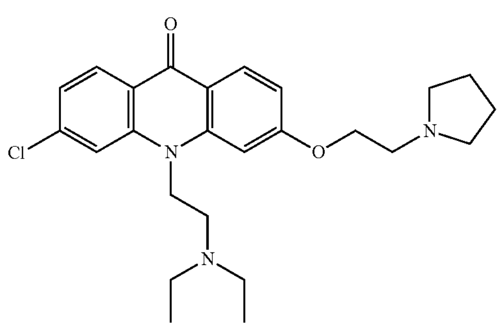 [SMILES: CCN(CC)CCn1c2cc(Cl)ccc2c(=O)c2ccc(OCCN3CCCC3)cc21] | 50 | 116 | TBD | TBD |
| T9.5 | 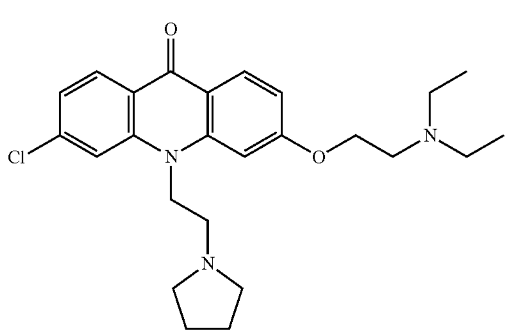 [SMILES: CCN(CC)CCOc1ccc2c(=O)c3ccc(Cl)cc3n(CCN3CCCC3)c2c1] | 33 | 60 | TBD | TBD |

TABLE 4-continued

In vitro antimalarial activity, cytotoxicity, and heme-binding affinity, of selected acridones.

| DRUG | Structure | $IC_{50}$ (nM) P. falciparum D6* | Dd2* | $IC_{50}$ (nM)[a] MSLCs | Heme-binding $K_a^b$ ($10^4 M^{-1}$) |
|---|---|---|---|---|---|
| T10.5 | [structure] | 637 | 595 | TBD | TBD |
| T11.5 | [structure] | 196 | 359 | TBD | TBD |
| QN | [structure] | 19 | 87 | TBD | TBD |

TBD: to be determined.
*,[a],[b]See Table 2 footnote for details.
[†]QN: quinine.

Example 4

Figure 2:
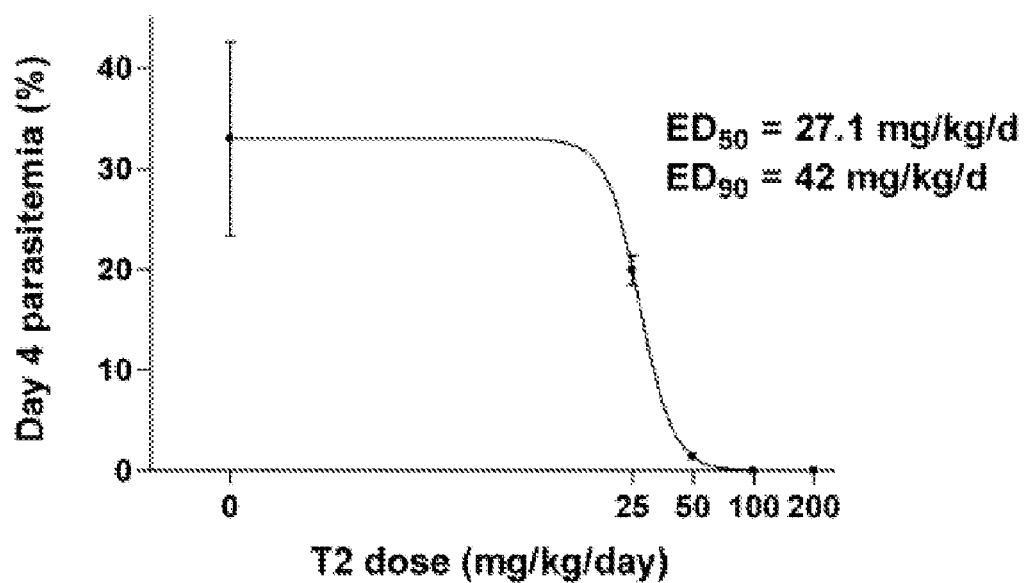
FIG. 2 illustrates the in vivo antimalarial activity of a disclosed antimalarial acridone (T2) against P. yoelii (K) in female CF-1 mice in a 4 day suppressive trial.

This example describes evaluation of the in vivo antimalarial efficacy of the disclosed acridones against CQ-sensitive P. yoelii (strain K) in female CF-1 mice. Illustrated in FIG. 2, are the results of a 4-day suppressive test with acridone T2 (3-(2-diethylaminoethoxy)-6-chloro-9-acridone)) in PBS administered intragastrically (ig) by gavage one hour after infection and then once daily, 24, 48 and 72 hours later. The T2 acridone exhibited excellent parasite inhibition and oral bioavailability with an $ED_{50}$ of 27.1 mg/kg, and $ED_{90}$ of 42 mg/kg. A dose of 200 mg/kg/day T2 completely suppressed parasitemia as assessed 24 hours after the last dose, and all of the four mice in that group remained parasite-free to the end of the observation period.

Example 5

This example describes the assessment of curative efficacy of acridone T2 (2-(2-diethylaminoethoxy)-6-chloro-9-acridone) in an in vivo model wherein treatment is started only after infection is patent (i.e., parasitemia is evident). For these studies, $5 \times 10^6$ P. yoelii (K) parasites were injected intravenously (iv) into naïve mice. Forty-eight hours later, parasitemia rose to 3-5%, and T2 was given intraperitoneally (ip) at 16 mg/kg, 64 mg/kg, and 256 mg/kg or ig (256 mg/kg only) once daily for three consecutive days. Blood smears were collected 24 hours after the last treatment. T2 brought about a rapid reduction in parasitemia in this regimen, with $ED_{50}$ (ip) of 38 mg/kg/day and $ED_{90}$ (ip) of 66 mg/kg/day. Enteral and parental dosing could only be compared at 256 mg/kg/day, but at that dose there was equal efficacy. There was a >99.9% reduction in parasitemia in all animals given 256 mg/kg/day (both ig and ip), and all were without evident parasitemia at 30 days. T2 exhibited similar efficacy by gavage against patent *P. berghei* (ANKA) infection ($ED_{50}$=55 mg/kg/day).

Figure 3:
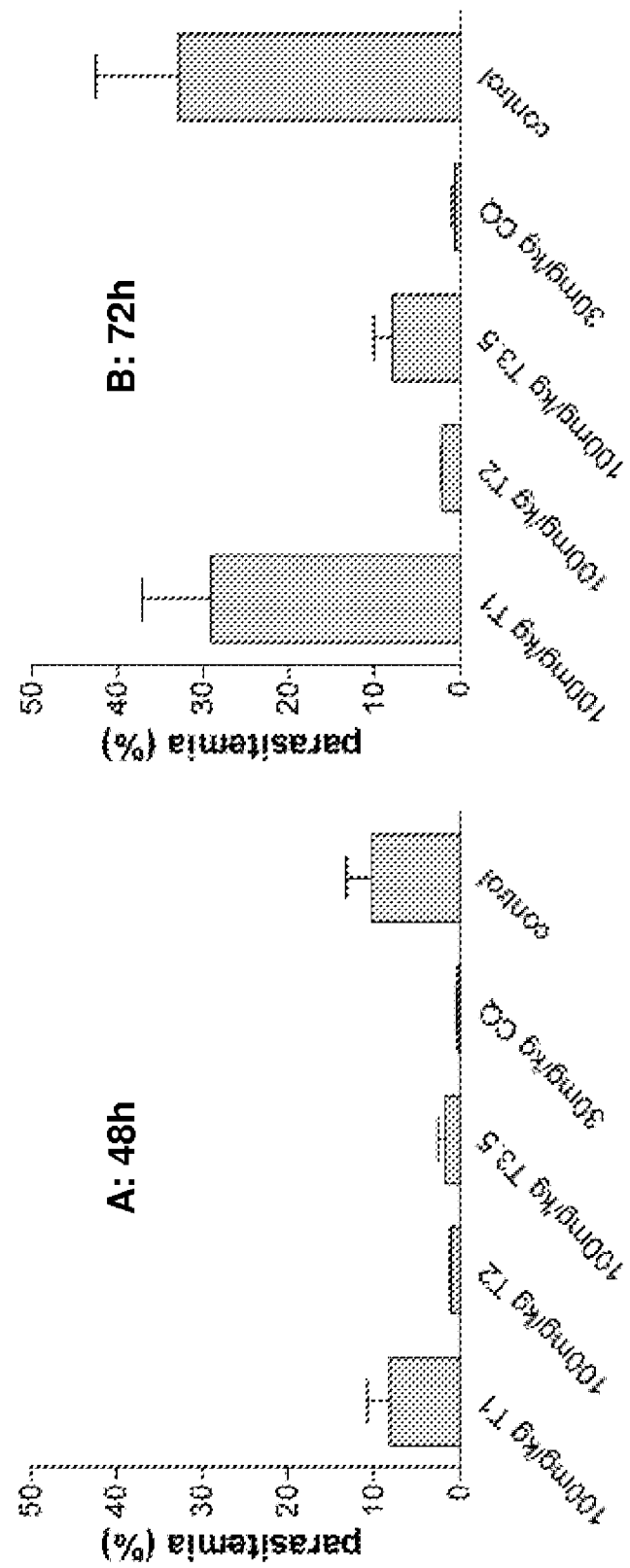
FIG. 3 illustrates the in vivo curative efficacy of a single ig dose of exemplary acridones vs. P. yoelii (K) patent infection, determined 48 and 72 hours after treatment.

The single-dose efficacy of acridone compounds also was assessed in vivo using ig treatment after patent infection. Test compounds were administered as a single dose at 100 mg/kg (30 mg/kg for CQ) 24 hours after *P. yoelii* infection, and blood smears were collected 48 and 72 hours post-treatment. The results for 3 acridone derivatives as well as CQ are displayed in FIG. 3. Compared with controls, T2 (HCl salt), T3.5 (di-HCl salt) and CQ each reduced parasitemia by more than 80% at 48 hours, and greater than 90% reduction persisted at 72 hours after T2 administration. Due to the difference in the molecular weight between the salts of T2 and T3.5, the apparent superiority of T2 over T3.5 at 72 hours may only reflect a lack of molar equivalence in dosing, rather than pharmacokinetic and/or pharmacodynamic advantages of T2). The results also validate this single-dose rodent model as a useful tool for primary screening of in vivo antimalarial activity, and for assisting the process of lead optimization of acridone derivatives. Patent infection before treatment, single-dose treatment and serial observations provide valuable information with minimal resource use that should be predictive of ultimate efficacy, curative effect, bioavailability, toxicity, and pharmacokinetic/pharmacodynamic properties.

It is noteworthy that the highest doses in the in vivo tests (200 mg/kg/day×4 days and 256 mg/kg/day×3 days) were well tolerated. Considering the $ED_{50}$ values, the lack of evident toxicity forecasts a favorable in vivo therapeutic safety index for acridone derivatives.

Example 6

This example describes the evaluation of chemosensitization and synergistic effects produced by administration of the disclosed acridones in combination with other chemotherapeutic agents, including anticancer, antibiotic, antiviral, and antiparasitic agents, such as antimalarial agents.

Antimalarial drug combinations can be assessed in a number of ways. For example, the response modification index (RMI) can be calculated by the following formula: RMI=$IC_{50}$ of drug A in the presence of drug B/$IC_{50}$ of drug A alone, where drug A is an existing antimalarial and B is a single sub-inhibitory concentration of the acridone candidate. An RMI less than 1.0 represents chemosensitization and possible synergy. A second method of evaluating combination therapies is Fractional Inhibitory Concentration, (e.g., $FIC_{50}$= [$IC_{50}$ of Drug A in the presence of a fixed amount of Drug B]/[$IC_{50}$ of Drug A alone]). RMI and FIC are helpful measures for side-by-side comparison of multiple chemosensitizer drugs at fixed concentrations, but neither distinguishes between additive and synergistic effects, or describes effects over a wide concentration range. Standard FIC indices (FIC of Drug A+FIC of Drug B) distinguish synergistic, additive and antagonistic interactions, but are dependent on the correct estimation of the expected effect of the fixed test drug.

In one embodiment, synergism is assessed herein using fixed-ratio combinations that provide information over a wide range of drug concentrations. In this method, the two drugs are mixed in an appropriate ratio, serial dilutions of the combined solution are used for testing, and results compared to each drug alone. Specifically, to determine synergy, the acridone is tested in combination with a second drug using a modification of the fixed-ratio method described by Fivelman et al. (See, Fivelman et al., *Antimicrob. Agents Chemother.* 48, 4097-4102 (2004) and Winter et al., *Antimicrob. Agents Chemother.* 41, 1449-1454 (1997), both references incorporated herein, in their entirety, by reference). In this method, after $IC_{50}$ determination for all test drugs, stock solutions were prepared of each drug at concentrations such that the final concentration in the 96-well plate drug susceptibility assay after 4-5 2-fold dilutions will approximate the $IC_{50}$. If these stock solutions were termed Drug A and Drug B, then six final stock solutions were prepared from this initial stock: Drug A alone, Drug B alone, and volume:volume mixtures of Drug A and B in the following ratios: 4:1, 3:2, 2:3, and 1:4. Two-fold dilutions of each of the six final stock solutions were done robotically across a 96-well plate in quadruplicate. Subsequent steps were typical of standard drug-susceptibility methods. Initial data analysis yielded the intrinsic dose-response curve for each drug alone, and four different fixed: ratio combination dose-response curves. The data pointed from all six curves were then analyzed using Calcusyn software (commercially available from BioSoft, Cambridge, UK) for determination of synergy. Output from this analysis included FIC values used to plot isobolograms as well as a rigorously determined synergy index, termed the combination index (CI) (Calcusyn). $FIC_{50}$ isobolograms, CI's and tabulation of $IC_{90}$ component drug concentrations were reported.

Figure 4:
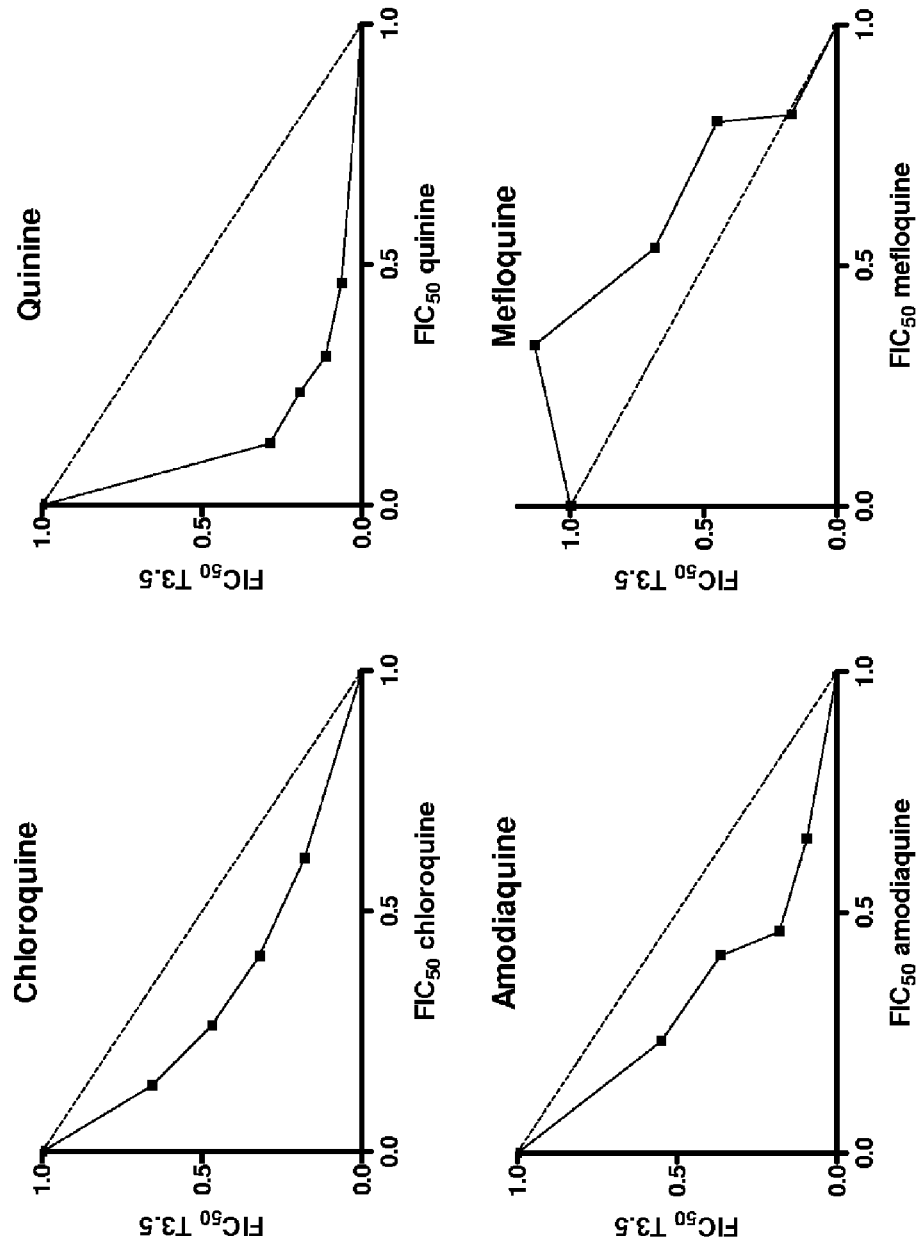
FIG. 4 includes isobolograms charting the efficacy of selected quinolines in combination with the antimalarial acridone T3.5 in vitro against multi drug resistant (MDR) P. falciparum (Dd2), wherein values below the diagonal (additive) line indicate synergism.

Using this method, T3.5 (3-(2-diethylaminoethoxy)-6-chloro-10-(2-diethylaminoethyl)-9-acridone) was evaluated in combination with the known antimalarial quinolines chloroquine, quinine, amodiaquine and mefloquine. The results are depicted in four isobolograms in FIG. 4.

Figure 5:
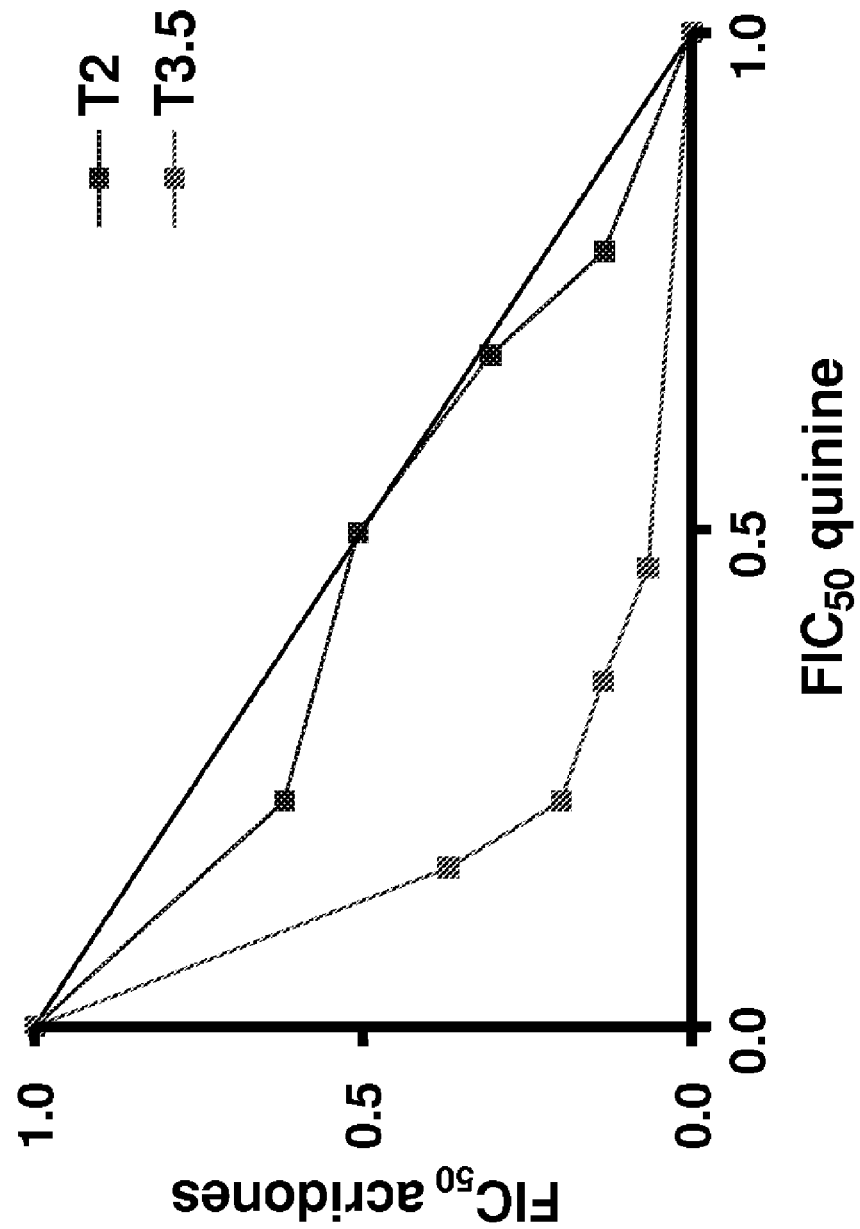
FIG. 5 is an isobologram charting the efficacy of quinine in combination with the antimalarial acridones T2 (top line) or T3.5 (bottom line) in vitro against MDR P. falciparum Dd2.

The combinations of the acridones T3.5 and T2 with quinine were assessed for synergism. The results are charted in the isobologram of FIG. 5. With reference to FIG. 5, values below the diagonal (additive) line indicate synergism, demonstrating synergism between quinine and T3.5, but not quinine and T2.

Figure 6:
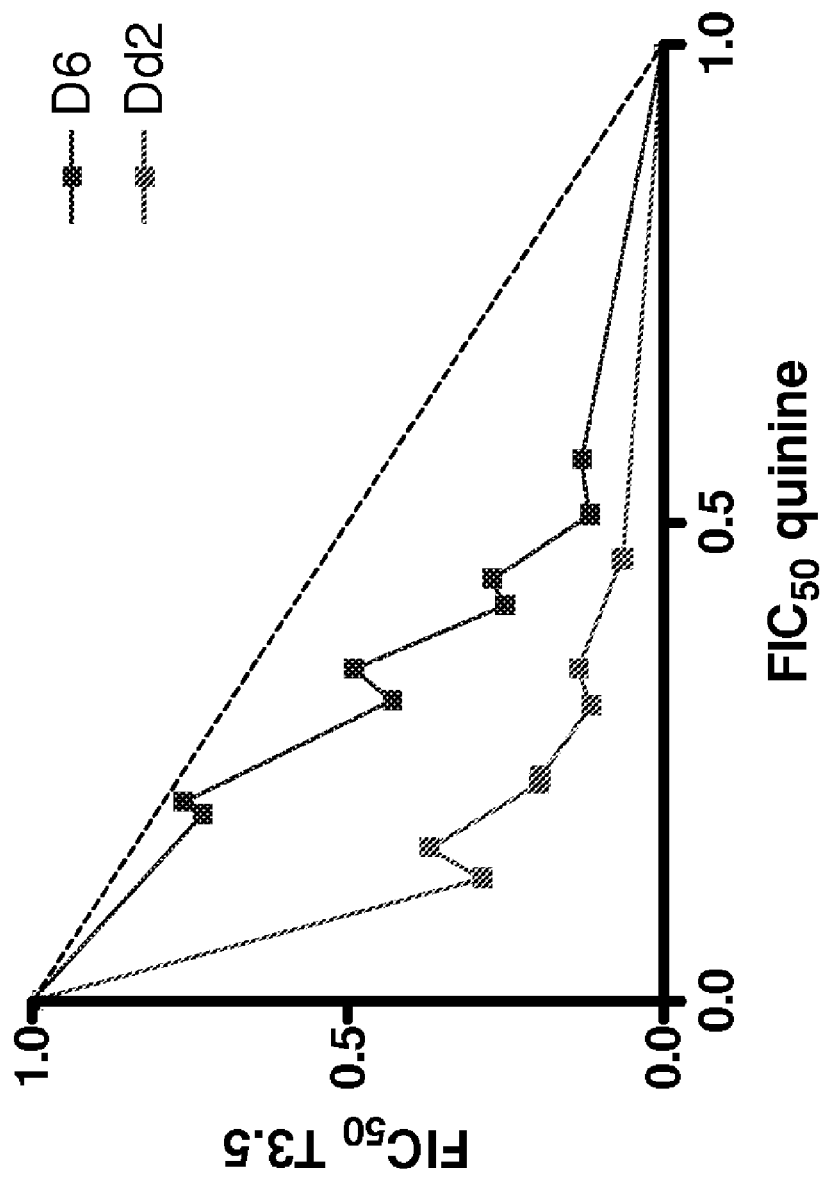
FIG. 6 is an isobologram charting the efficacy of quinine in combination with T3.5 in vitro against CQ-sensitive (D6 top line) and MDR (Dd2 bottom line) P. falciparum demonstrating synergy of the combination, particularly against MDR P. falciparum.
Figure 7:
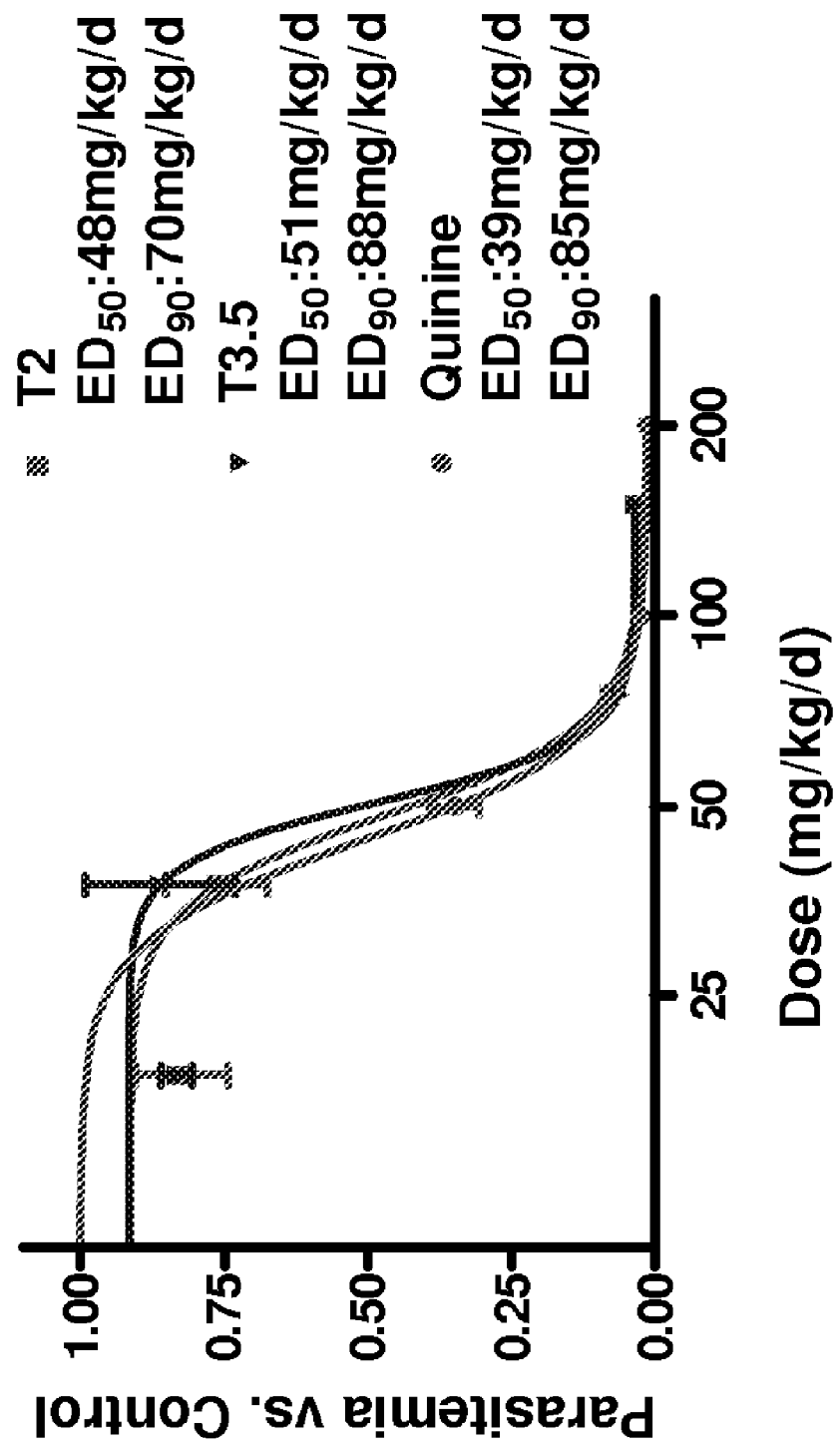
FIG. 7 is a graph showing in vivo antimalarial activity of acridones T2 and T3.5 as well as quinine against P. yoelii.

FIG. 6 is an isobologram charting the efficacy of quinine in combination with T3.5 in vitro against CQ-sensitive (D6) and MDR (Dd2) *P. falciparum*. Values below the diagonal (additive) line indicate synergism between quinine and T3.5 against both strains. The results illustrated in FIG. 6, demonstrate 90% growth inhibition of quinine-resistant Dd2 was achieved at low concentrations (20-200 nM T3.5 in combination with 7-70 nM quinine), a significant advance toward clinical value.

Example 7

This example describes visual evidence that acridones disclosed herein form soluble complexes with heme under mildly acidic conditions. As described in Example 1, tricyclic xanthones formed soluble complexes with heme, preventing heme precipitation in vitro. Employing the same assay conditions, heme was mixed with T2 or T3.5 under mildly acidic conditions (25 mM phosphate buffer, pH 4.8) and monitored. As in the case of the xanthones, after the first 30 minutes at room temperature it was evident that T2 and T3.5 form soluble complexes with heme under the pH conditions that exist in the digestive vacuole. Both T2 and T3.5 prevent the formation of heme aggregates, a process that is normally spontaneous at this pH. Without being limited to theory, it is believed that for some compounds inhibition of heme aggregation in vitro can be correlated with inhibition of hemozoin formation in vivo. This straightforward in vitro test can be used to provide a preliminary assessment of antimalarial potential of antimalarial acridones. It is noteworthy that CQ fails to prevent heme aggregation in this assay, a result probably reflecting substantive differences in affinity, binding geometry and other factors.

Example 8

This example describes a general synthetic approach to the disclosed acridone compounds. The acridone core is assembled in according to Scheme 1 using the classic Ullman copper-mediated coupling reaction. With reference to the variable groups, X, Y, R¹ and R are as disclosed herein above, and Z represents H or a protected functional group, such as a masked group G. Ullman coupling of a suitable 2-chlorobenzoic acid derivative 10 with an appropriately substituted aniline derivative 20 gives diphenyl amine 30. Ring closure under acidic conditions yields tricyclic acridone 40. Various acridone derivatives can be prepared from tricyclic acridone 40, for example, the 10-position nitrogen is alkylated with alkyl halides to produce N-substituted acridone 50.

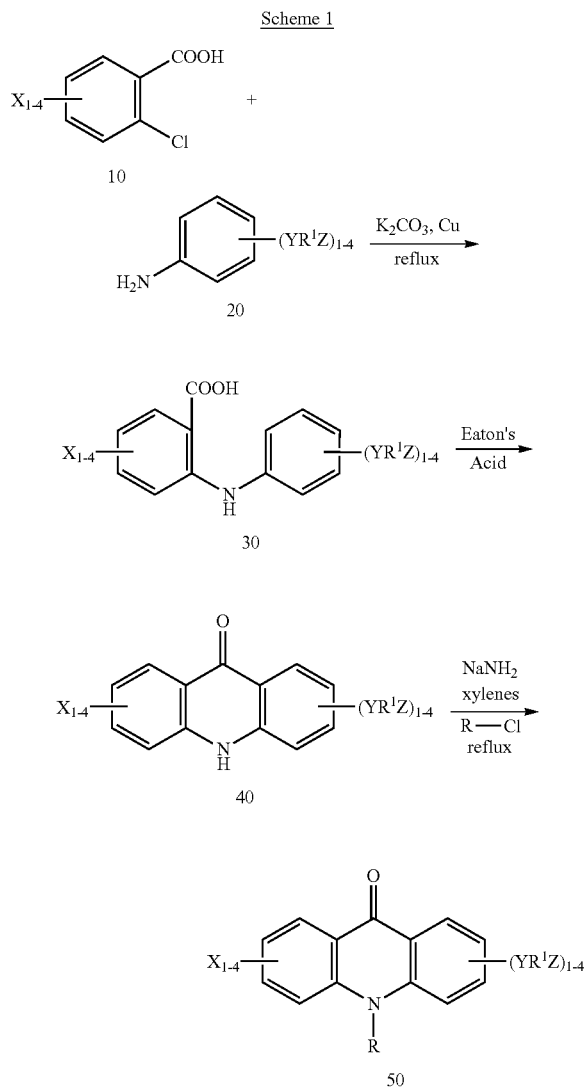

Compounds 40 and 50 can be further functionalized. For example when one of YR¹Z represents an alkoxy group, such as a methoxy group, the methoxy group can be cleaved to yield free phenols 60 and 70, for example as set forth in the Scheme 2. With continued reference to Scheme 2, such phenolic compounds can be further derivatized, for example compounds 60 and 70 can be alkylated with a haloalkyl group, such as a dibromoalkyl group compound to give compounds 80 and 90, respectively. Acridone derivatives 80 and 90 can be further functionalized, for example by alkylating a secondary amine to give compounds 100 and 110.

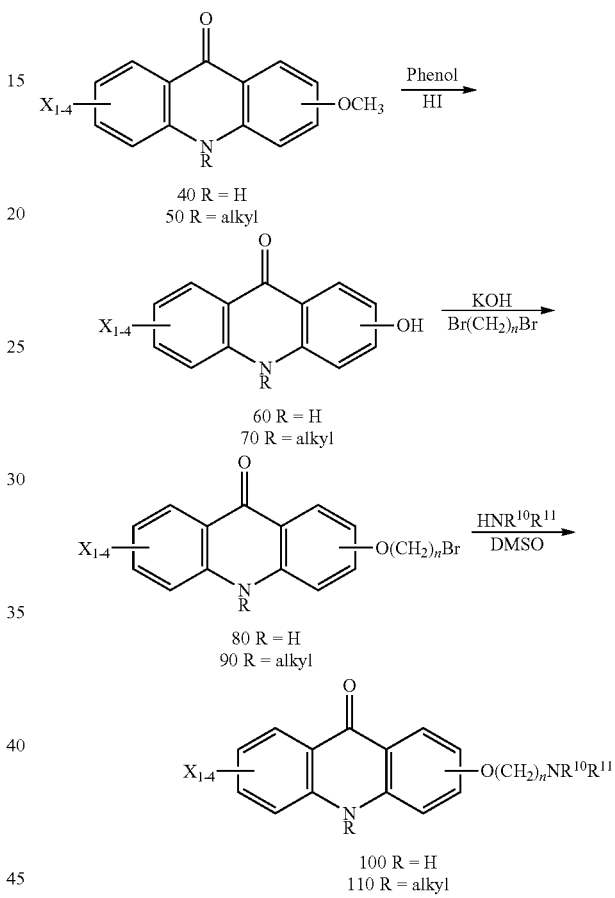

T 3.5 (3-(diethylamino-ethoxy)-6-chloro-N-10-diethylaminoethyl-9-acridone) was prepared according to the schemes above, with the final product obtained by reacting 3-hydroxy-6-chloro-9-acridone with 2 equivalents of (2-chloro-ethyl)-diethyl-amine (as the hydrochloride salt) in acetone with potassium carbonate at reflux for 12 hours. After this period the solvent was removed in vacuo and the residue was taken up in hexane whereupon it crystallized on standing and evaporation, and in high yield, ca. 50 to 100% of theoretical yield.

Similarly, T2 (3-diethylamino-ethoxy)-6-chloro-9-acridone) was prepared according to the schemes above, with the final product being obtained by reacting 3-hydroxy-6-chloro-9-acridone with one equivalent of (2-chloro-ethyl)-diethyl-amine (as the hydrochloride salt) in ethanol and in the presence of a 1.5 equivalent excess of potassium hydroxide and heated at reflux for 12 hours. After this period the reaction vessel was taken to dryness and the residue was taken into a mixture of ethanol and water. Upon cooling the desired product fell out of solution and was filtered and dried in this high yielding reaction, ca. 50 to 100% of expected yields.

Example 9

This example describes evaluation of acridones in rodent models of blood-stage malaria. Initial testing of the in vivo antimalarial efficacy of gavage-administered T2 (HCl salt) against CQ sensitive *P. yoelii* (K) in the standard 4-day suppressive test (1) revealed excellent parasite inhibition ($ED_{50}$ 27.1 mg/kg, $ED_{90}$ 42 mg/kg, complete suppression at 200 mg/kg/day).

Figure 8:
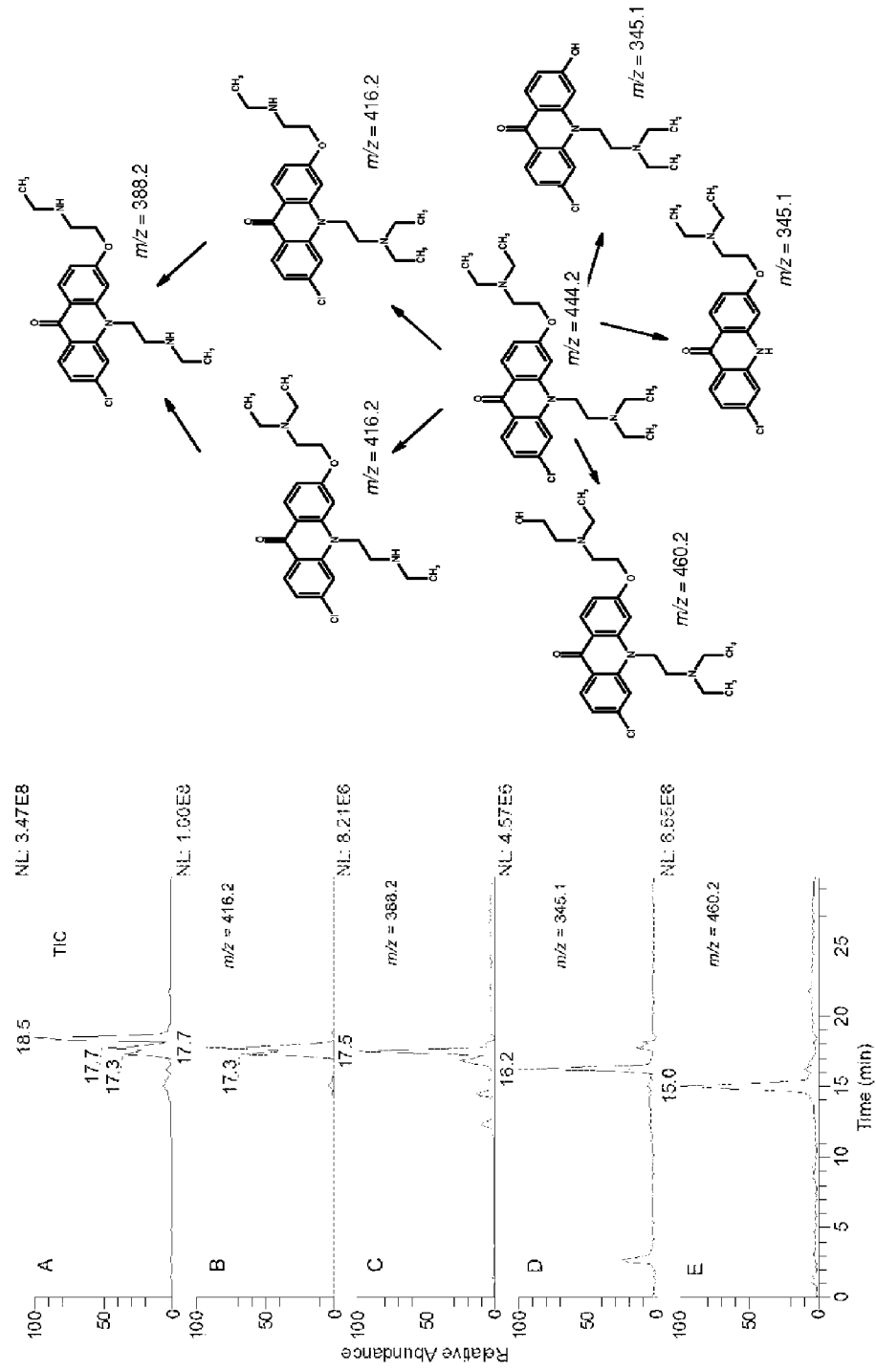
FIG. 8 (panels A-E) shows metabolite profiles of the acridone T3.5 in murine S-9 with NADPH for 60 minutes.

In an adaptation of the standard 6-day Thompson test, three once-daily doses were administered to mice starting 2 days after infection, when parasitemia was ~3%, and efficacy was measured by determining parasitemia from blood smears obtained 1 day after the third and final dose. Using gavage (ig) dosing in this model, the $ED_{50}$ and $ED_{90}$ of T2, T3.5, and QN are comparable against *P. yoelii* (K) (FIG. 8). T2 has also been assessed after intraperitoneal (ip) dosing, with comparable results ($ED_{50}$ and $ED_{90}$=38 and 66 mg/kg/day, respectively), and against *P. berghei* (ANKA) (55 and 80 mg/kg/day, respectively). T2 testing at 256 mg/kg/day resulted in long-term cure.

Example 10

This example evaluates the prophylactic efficacy of the acridone T2. T2 was evaluated in a murine *P. yoelii* sporozoite-induced malaria model to determine prophylactic efficacy.

Mice were treated with 160 mg/kg ig, on days −1, 0, and 1 with injection of 250,000 sporozoites on day 0. Blood smears on days 6, 11, and 14 showed all 5 treated animals to be parasite-free, a result comparable to that of primaquine in the same model. No toxicity was observed.

Drug doses administered include 300 mg/kg in a single dose (T2, T2.2, T3.5, T7.5, T8.5, T9.5), 256 mg/kg/day×3 days (T1, T2), and 200 mg/kg/day×4 days (T2, T3.5). Other than 10% weight loss in animals receiving T2 at 256 mg/kg/day×3 days, there has been no general toxicity noted in mice treated with any of the candidate acridones, at any dose, and our initial cured animals are alive and well nearly a year after treatment. An in vitro screen for cytotoxicity in murine splenic lymphocytes shows that the $IC_{50}$ of CQ is 1.3 µM, whereas the $IC_{50}$ of most candidate acridones described in this proposal exceed 25 µM.

Example 11

This example provides an in vitro assessment of T2 and T3.5 activity in a model using cloned biogenic amine transporters. Unlike tricyclic antidepressants and cocaine positive controls, the acridones had no significant affinity for serotonin, dopamine, or norepinephrine transporters (Table 5).

TABLE 5

Effects of drugs on inhibition of radioligand [$^{125}$I]RTI-55 binding to the recombinant human dopamine (hDAT), serotonin (hSERT), and norepinephrine (hNET) transporters stably expressed in human embryonic kidney (HEK) cells.

| Compound | [$^{125}$I]RTI-55 Binding HEK-hDAT $K_i$ (nM) | [$^{125}$I]RTI-55 Binding HEK-hSERT $K_i$ (nM) | [$^{125}$I]RTI-55 Binding HEK-hNET $K_i$ (nM) |
|---|---|---|---|
| T2 | >10,000 | >10,000 | 5848.50 |
| T3.5 | >10,000 | 2292.72 | >10,000 |
| Mefloquine | >10,000 | 90.02 | 3875.09 |
| Cocaine* | 296.12 | 198.72 | 655.94 |

*Cocaine was used as a positive control.

Example 12

This example provides morphological changes in acridone treated parasites. In vitro human PRBCs (*P. falciparum* D6, Dd2), ex vivo mouse PRBCs (*P. yoelii* (Kenya) and in vivo mouse PRBCs (*P. yoelii* (Kenya), *P. berghei* [ANKA gfp+, luc+]) all demonstrate failure of acridone-exposed parasites to progress from trophozoite to schizont stage. Compared to drug-free controls, T1-treated late trophozoites appear pale staining with loss of intracellular definition and fragmented hemozoin (FIG. 9). When drug treatment followed high parasitemia (as in FIG. 9), many such abnormal parasites were evident 24 hr after cessation of drug treatment but then were rapidly cleared over the following 24-48 hours, indicating non-viability. These preliminary evaluations of blood smears by light microscopy indicate that acridones cause alterations in parasite morphology and viability.

*P. falciparum* Dd2 MDR parasited red cells were synchronized to the ring stage by sorbitol lysis and incubated the cells in the presence or absence of 300 nM T3.5. As compared to controls after exposure to T3.5, the PRBC cytoplasm was more basophilic and visible hemozoin was markedly diminished. FIG. 10 shows images of control vs. drug treated parasites after 36 hours of incubation. *P. yoelii* infected mice treated with T3.5 harbor PRBCs that lack hemozoin. Taken together these observations are consistent with the notion that T3.5 blocks hemozoin formation in infected cells.

Example 13

This example shows a pattern of synergy with quinoline antimalarials: a property of the T3.5 type of acridones. In vitro isobolar analysis demonstrates that T3.5 is a potent chemosensitizer, synergistic in combination with CQ, QN or amodiaquine, but not with mefloquine, against the MDR Dd2 clone while there is no evidence of synergy in the additive interaction between T2 and QN (see FIG. 11). Screening of T3.5 and other acridones by determination of RMI indicates chemosensitizing action throughout the group (see Table 6).

TABLE 6

In vitro chemosensitizing effects of acridones against CQS (D6) and MDR (Dd2) strains of *P. falciparum*.

| Drug Combination | D6 $IC_{50}$ (nM) | D6 $RMI^a$ | Dd2 $IC_{50}$ (nM) | Dd2 $RMI^a$ | Drug Combination | D6 $IC_{50}$ (nM) | D6 $RMI^a$ | Dd2 $IC_{50}$ (nM) | Dd2 $RMI^a$ |
|---|---|---|---|---|---|---|---|---|---|
| QN alone | 20 | — | 87 | — | CQ alone | 8.4 | — | 124 | — |
| QN + 50 nM T3.5 | 7.5 | 0.38 | 11 | 0.13 | CQ + 50 nM T3.5 | 3.7 | 0.44 | 32 | 0.26 |

TABLE 6-continued

In vitro chemosensitizing effects of acridones against CQS (D6) and MDR (Dd2) strains of *P. falciparum*.

| Drug Combination | D6 IC$_{50}$ (nM) | RMI[a] | Dd2 IC$_{50}$ (nM) | RMI[a] | Drug Combination | D6 IC$_{50}$ (nM) | RMI[a] | Dd2 IC$_{50}$ (nM) | RMI[a] |
|---|---|---|---|---|---|---|---|---|---|
| QN + 50 nM T2.1.5 | 7.1 | 0.36 | 8.0 | 0.09 | CQ + 50 nM T2.1.5 | 6.7 | 0.79 | 47 | 0.38 |
| QN + 50 nM T2.2.5 | 5.4 | 0.28 | 12 | 0.13 | CQ + 50 nM T2.2.5 | 3.1 | 0.37 | 32 | 0.26 |
| QN + 50 nM T4.5 | 4.2 | 0.22 | 9.6 | 0.11 | CQ + 50 nM T4.5 | 2.9 | 0.35 | 39 | 0.31 |
| QN + 50 nM T6.5 | 4.0 | 0.20 | 7.8 | 0.09 | CQ + 50 nM T6.5 | 2.0 | 0.24 | 28 | 0.23 |
| QN + 50 nM VP[b] | 21 | 1.1 | 85 | 0.98 | CQ + 50 nM VP[b] | 8.3 | 0.99 | 118 | 0.95 |

QN: quinine
[a]RMI: IC$_{50}$ of QN (or CQ) in combination with chemosensitizers/IC$_{50}$ of QN (or CQ) alone.
[b]VP: verapamil.

Example 14

This example provides a demonstration of in vivo synergism between T3.5 and quinine. In vivo synergism was assessed using the 6-day Thompson test in mice infected with QN-sensitive *P. yoelii* (K), comparing the efficacy of T3.5 alone, QN alone and T3.5:QN combinations (Table 7). Dosages were established using a rigorous fixed-ratio combination dosing protocol and results were assessed using Calcusyn software to determine synergy. As in the case of the in vitro combination, there was evident in vivo synergism. At the ED$_{50}$, ED$_{75}$ and ED$_{90}$ effect levels, the Combination Index (CI) was <0.6, indicating definite and significant synergy. More clinically relevant than this measure of synergy, the dose combination resulting in 90% inhibition of growth suggests that substantial dose reductions of the individual drugs can be achieved. Alone, the ED$_{90}$ of T3.5 and QN were 88 and 85 mg/kg/day, respectively; only 24 mg/kg/day of each in combination produced the same result.

TABLE 7

Synergism between T3.5 & quinine in vivo vs. patent infections of *P. yoelii* (quinine sensitive) in mice.

| | Dose (mg/kg/day) | | |
|---|---|---|---|
| Effect | T3.5 alone | Quinine alone | T3.5:Quinine Combination |
| ED$_{50}$ | 56 | 39 | 14:14 |
| ED$_{75}$ | 70 | 57 | 19:19 |
| ED$_{90}$ | 88 | 85 | 24:24 |

Example 15

This example investigates the metabolic stability and fate of T3.5 in the presence of NADPH and a murine hepatic S9 fraction. Hepatic S-9 fractions were incubated with 50 µM T3.5 in the presence of NADPH (1 mM) for 10, 30 and 60 min. HPLC was conducted with a Hypersil Gold column that is stable at high pH. As a result, a solvent system at pH 10.5 was used and excellent peak shape was obtained for T3.5 (calculated pKa of 9.5). Despite the high pH, T3.5 (a retention time of 18.5 min in Panel A, FIG. 12) exhibited an abundant molecular ion in the positive mode [M+H]$^+$ at m/z 444.2. The full scan mass spectrum had the isotopic ratio expected for the chlorine substituted acridone ring. FIG. 12 shows the extracted ion chromatograms for a series of possible P450-dependent metabolites of T3.5 produced in the S-9 incubation with NADPH. The most abundant metabolites were de-ethylated products monitored at m/z 416.2 (loss of m/z=28) with retention times of 17.3 and 17.7 min. The two unresolved peaks most likely represent de-ethylation of the tertiary amine on each side chain.

A second de-ethylation also occurred with the prolonged incubation as evidenced by the peak at 17.5 min when monitored at m/z 388.1 (loss of m/z=56). Another dealkylated metabolite was monitored at m/z 345.1 and corresponds to the loss of the triethylamine side chain (loss of m/z=99) from the acridone ring. The dealkylation could occur from either the aryl ether side chain or from the acridone ring nitrogen. The later would result in the production of the active compound T2. Extensive de-ethylation suggests that if the secondary amine metabolite is active, the pharmacodynamic half-life could be much longer than the parent compound as active metabolites would be produced. In addition to the dealkylated products, a hydroxylated metabolite was also detected by monitoring at m/z 460.2 (addition of m/z=16). The hydroxylation could occur on the acridone ring or on one of the primary carbons on the ethylamine side chains. Further MS/MS experiments will help establish the site of hydroxylation.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for inhibiting or treating a parasitic infection in a subject, comprising administering to a subject a therapeutically effective amount of a compound according to the formula

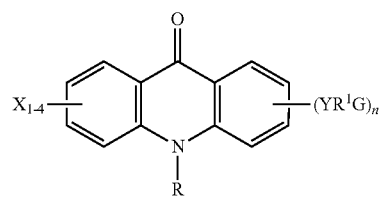

or a pharmaceutically acceptable salt thereof;

wherein R is —R²NR³R⁴ or —R¹G;
X is halogen, haloalkyl, —OR⁵ or —YR¹G;
n is 1-4;
Y is —CH₂—, —CH₂O—, —O—, —N(R⁶)— or —S—;
R⁵ is lower alkyl, haloalkyl or —R⁷NR⁸R⁹;
R¹, R² and R⁷ independently are optionally substituted alkyl;
G is —NR¹⁰R¹¹, halogen or fluoroalkyl;
R³, R⁴, R⁶, R⁸ and R⁹ independently are H, lower alkyl, or aralkyl;
R¹⁰ and R¹¹ independently are H, lower alkyl, aralkyl or together form an aliphatic or aromatic ring optionally including one or more additional heteroatoms.

2. The method of claim 1, wherein the compound is administered prophylactically.

3. The method of claim 1, wherein the therapeutically effective amount is from about 1 to about 50 mg/kg administered at least one time.

4. The method of claim 1, wherein the parasitic infection is malaria.

5. The method of claim 1, wherein at least one of the causes of the malaria is *P. falciparum* infection.

6. The method of claim 5, wherein the compound is administered in a malaria-curative dose over 1-10 days.

7. The method of claim 6 wherein the compound is administered in a malaria-curative dose over 2-5 days.

8. The method of claim 1, wherein the parasitic infection comprises toxoplasmosis.

9. The method of claim 2, wherein the parasitic infection comprises toxoplasmosis.

10. A method for potentiating a primary drug to treat a multidrug resistant disorder in a subject wherein the multidrug resistant disorder is a parasitic infection, comprising administering to the subject an effective amount of a compound according to the formula

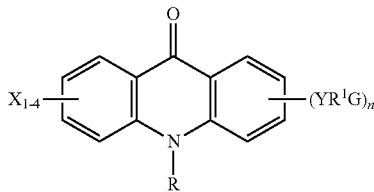

or a pharmaceutically acceptable salt thereof;
wherein R is —R²NR³R⁴ or —R¹G;
X is halogen, haloalkyl, —OR⁵ or —YR¹G;
n is 1-4;
Y is —CH₂—, —CH₂O—, —O—, —N(R⁶)— or —S—;
R⁵ is lower alkyl, haloalkyl or —R⁷NR⁸R⁹;
R¹, R² and R⁷ independently are optionally substituted alkyl;
G is —NR¹⁰R¹¹, halogen or fluoroalkyl;
R³, R⁴, R⁶, R⁸ and R⁹ independently are H, lower alkyl, or aralkyl;
R¹⁰ and R¹¹ independently are H, lower alkyl, aralkyl or together form an aliphatic or aromatic ring optionally including one or more additional heteroatoms.

11. The method of claim 10, wherein the parasitic infection is *Entamoeba histolytica*, trypanosomiasis, leishmaniasis, toxoplasmosis, or malaria.

12. A method for potentiating a primary drug to treat a parasitic protozoa multidrug resistance, comprising: exposing multidrug resistant protozoa to an effective concentration of a compound according to the formula

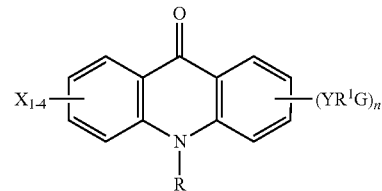

or a pharmaceutically acceptable salt thereof;
wherein R is —R²NR³R⁴ or —R¹G;
X is halogen, haloalkyl, —OR⁵ or —YR¹G;
n is 1-4;
Y is —CH₂—, —CH₂O—, —O—, —N(R⁶)— or —S—;
R⁵ is lower alkyl, haloalkyl or —R⁷NR⁸R⁹;
R¹, R² and R⁷ independently are optionally substituted alkyl;
G is —NR¹⁰R¹¹, halogen or fluoroalkyl;
R³, R⁴, R⁶, R⁸ and R⁹ independently are H, lower alkyl, or aralkyl;
R¹⁰ and R¹¹ independently are H, lower alkyl, aralkyl or together form an aliphatic or aromatic ring optionally including one or more additional heteroatoms.

13. The method of claim 12, wherein the protozoa are trypanosomes.

14. The method of claim 1 wherein the compound has the formula

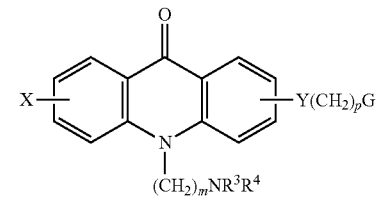

wherein m and p independently are from 2 to 10.

15. The method of claim 14, wherein m and p independently are from 2 to 5.

16. The method of claim 1, wherein the compound has the formula

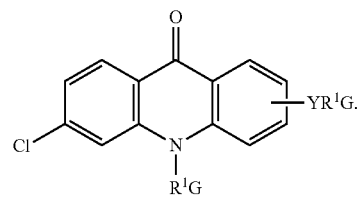

17. The method of claim 1, wherein X is halogen, R is —(CH₂)ₘNR³R⁴, and —YR¹G is —O(CH₂)ₙNR¹⁰R¹¹, wherein m is from 2 to 10 and n is from 2 to 5.

18. The method of claim 17, wherein X is Cl, R is —(CH₂)₂N(Et)₂, and —YR¹G is —O(CH₂)ₙN(H)(—C(CH₃)₃).

19. The method of claim 18, wherein —YR¹G is —O(CH₂)₃N(H)(—C(CH₃)₃).

20. The method of claim 1, wherein R is —(CH₂)ₘNR³R⁴, and —YR¹G is —O(CH₂)ₙNR¹⁰R¹¹, wherein m is from 2 to 10 and n is from 2 to 5.

21. The method of claim 1, wherein R is —(CH$_2$)$_m$NR$^{10}$R$^{11}$, wherein m is from 2 to 10.

22. The method of claim 1, —YR$^1$G is —O(CH$_2$)$_n$NR$^{10}$R$^{11}$, wherein n is from 2 to 5.

23. The method of claim 16, wherein —YR$^1$G is —O(CH$_2$)$_3$N(H)(—C(CH$_3$)$_3$).

24. The method of claim 1, wherein there are two to four X groups.

25. The method of claim 24, wherein the X groups are each halogen.

26. The method of claim 1, wherein the compound has the formula

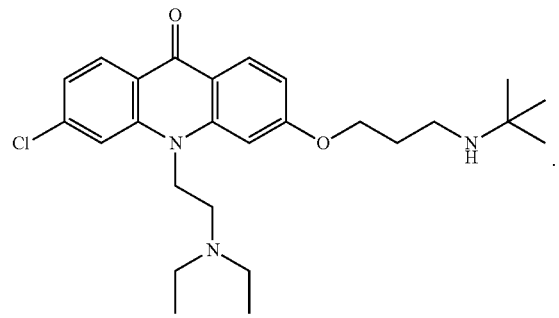 [SMILES: CCN(CC)CCn1c2cc(Cl)ccc2c(=O)c2ccc(OCCCNC(C)(C)C)cc21]

27. The method of claim 1, wherein the compound has the formula

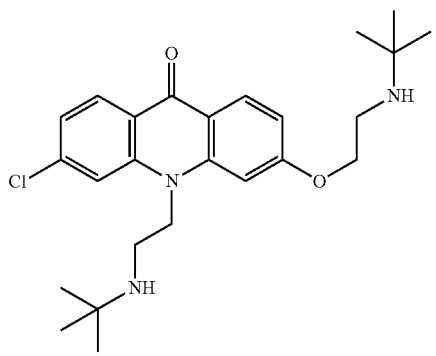

or

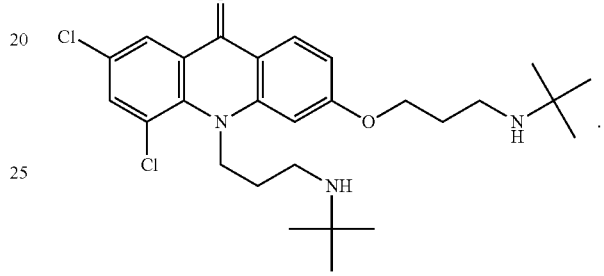

* * * * *